United States Patent
Schepis et al.

(10) Patent No.: US 10,512,413 B2
(45) Date of Patent: Dec. 24, 2019

(54) METHOD AND SYSTEM FOR IDENTIFICATION OF SOURCE OF CHRONIC PAIN AND TREATMENT

(71) Applicant: Avent, Inc., Alpharetta, GA (US)

(72) Inventors: Eric A. Schepis, Alpharetta, GA (US); Phillip A. Schorr, Cumming, GA (US); Joshua D. White, Atlanta, GA (US)

(73) Assignee: Avent, Inc., Alpharetta, GA (US)

( * ) Notice: Subject to any disclaimer, the term of this patent is extended or adjusted under 35 U.S.C. 154(b) by 272 days.

(21) Appl. No.: 15/501,445

(22) PCT Filed: Aug. 24, 2015

(86) PCT No.: PCT/US2015/046485
§ 371 (c)(1),
(2) Date: Feb. 3, 2017

(87) PCT Pub. No.: WO2016/032931
PCT Pub. Date: Mar. 3, 2016

(65) Prior Publication Data
US 2017/0215758 A1    Aug. 3, 2017

Related U.S. Application Data

(60) Provisional application No. 62/041,798, filed on Aug. 26, 2014.

(51) Int. Cl.
*A61B 5/00* (2006.01)
*A61B 5/0476* (2006.01)
(Continued)

(52) U.S. Cl.
CPC .......... *A61B 5/0476* (2013.01); *A61B 5/0484* (2013.01); *A61B 5/0538* (2013.01);
(Continued)

(58) Field of Classification Search
CPC ..... A61B 5/053; A61B 5/0538; A61B 5/0476; A61B 5/0484; A61B 5/4047
See application file for complete search history.

(56) References Cited

U.S. PATENT DOCUMENTS 3,682,162 A    8/1972  Colyer
4,515,168 A    5/1985  Chester et al.
(Continued)

FOREIGN PATENT DOCUMENTS

EP    0 823 265 A2    2/1998
WO    WO 01/12089 A1   2/2001

OTHER PUBLICATIONS

Apkarian et al., "Towards a theory of chronic pain", Prog. Neurobiol., vol. 87, No. 2, Feb. 2009, 33 pages.
(Continued)

*Primary Examiner* — Max F Hindenburg
(74) *Attorney, Agent, or Firm* — Dority & Manning, P.A.

(57) ABSTRACT

A method for identifying and treating a neural pathway associated with chronic pain via nerve stimulation and brain wave monitoring of a mammalian brain includes positioning a probe to stimulate a target nerve, wherein the target nerve is suspected of being a source of chronic pain; delivering a first nerve stimulation from the probe to the target nerve, wherein the first nerve stimulation is sufficient to elicit a chronic pain response in the brain; and monitoring for evoked potential activity in the brain as a result of the first nerve stimulation. The method can also include delivering second and third nerve stimulations to confirm the correct identification of the neural pathway and to treat the chronic pain, respectively. A system and apparatus for performing a procedure to identify and treat a nerve that is the source of chronic pain are also described.

17 Claims, 8 Drawing Sheets

(51) Int. Cl.
*A61B 5/0484* (2006.01)
*A61B 5/053* (2006.01)
*A61B 18/14* (2006.01)
*A61N 1/36* (2006.01)
*A61B 5/01* (2006.01)
*A61B 5/0402* (2006.01)
*A61B 5/0488* (2006.01)
*A61B 18/00* (2006.01)

(52) U.S. Cl.
CPC .......... *A61B 5/4047* (2013.01); *A61B 5/4824* (2013.01); *A61B 5/4848* (2013.01); *A61B 5/4893* (2013.01); *A61B 18/148* (2013.01); *A61N 1/36021* (2013.01); *A61B 5/01* (2013.01); *A61B 5/0402* (2013.01); *A61B 5/0488* (2013.01); *A61B 2018/00011* (2013.01); *A61B 2018/0091* (2013.01); *A61B 2018/00434* (2013.01); *A61B 2018/00577* (2013.01); *A61B 2018/00642* (2013.01); *A61B 2018/00702* (2013.01); *A61B 2018/00744* (2013.01); *A61B 2018/00791* (2013.01)

(56) References Cited

U.S. PATENT DOCUMENTS

| | | |
|---|---|---|
| 5,284,154 A | 2/1994 | Raymond et al. |
| 5,899,860 A | 5/1999 | Pfeiffer et al. |
| 5,928,158 A | 7/1999 | Aristides |
| 6,206,874 B1 | 3/2001 | Ubby et al. |
| 6,508,765 B2 | 1/2003 | Suorsa et al. |
| 6,618,626 B2 | 9/2003 | West, Jr. et al. |
| 7,216,001 B2 | 5/2007 | Hacker et al. |
| 7,306,596 B2 | 12/2007 | Hillier et al. |
| 7,340,300 B2 | 3/2008 | Christopherson et al. |
| 7,657,308 B2 | 2/2010 | Miles et al. |
| 7,689,292 B2 | 3/2010 | Hadzic et al. |
| 7,699,809 B2 | 4/2010 | Urmey |
| 7,715,925 B2 | 5/2010 | Hafer et al. |
| 7,799,021 B2 | 9/2010 | Leung et al. |
| 7,824,404 B2 | 11/2010 | Godara et al. |
| 7,905,840 B2 | 3/2011 | Pimenta et al. |
| 7,918,802 B2 | 4/2011 | Urmey |
| 7,942,826 B1 | 5/2011 | Scholl et al. |
| 7,959,577 B2 | 6/2011 | Schmitz et al. |
| 7,972,308 B2 | 7/2011 | Putz |
| 7,983,757 B2* | 7/2011 | Miyazawa ......... A61N 1/36071 607/45 |
| 7,991,463 B2 | 8/2011 | Kelleher et al. |
| 8,016,846 B2 | 9/2011 | McFarlin et al. |
| 8,066,702 B2 | 11/2011 | Rittman, III et al. |
| 8,068,912 B2 | 11/2011 | Kaula et al. |
| 8,092,456 B2 | 1/2012 | Bleich et al. |
| 8,147,421 B2 | 4/2012 | Farquhar et al. |
| 8,172,768 B2 | 5/2012 | Strother et al. |
| 8,206,312 B2 | 6/2012 | Farquhar |
| 8,518,036 B2 | 8/2013 | Leung et al. |
| 9,707,396 B2* | 7/2017 | Su ......... A61B 5/4255 |
| 2003/0088185 A1 | 5/2003 | Prass |
| 2004/0260358 A1 | 12/2004 | Vaughan et al. |
| 2005/0119653 A1 | 6/2005 | Swanson |
| 2005/0177202 A1 | 8/2005 | Classen et al. |
| 2006/0089551 A1 | 4/2006 | England |
| 2006/0089633 A1 | 4/2006 | Bleich et al. |
| 2006/0106376 A1 | 5/2006 | Godara et al. |
| 2007/0282217 A1 | 12/2007 | McGinnis et al. |
| 2008/0161803 A1 | 7/2008 | Oral et al. |
| 2008/0167646 A1 | 7/2008 | Godara et al. |
| 2008/0183188 A1 | 7/2008 | Carls et al. |
| 2008/0221473 A1 | 9/2008 | Calancie et al. |
| 2008/0249430 A1 | 10/2008 | John et al. |
| 2009/0018610 A1 | 1/2009 | Gharib et al. |
| 2009/0054804 A1 | 2/2009 | Gharib et al. |
| 2009/0299214 A1 | 12/2009 | Wu et al. |
| 2010/0010367 A1 | 1/2010 | Foley et al. |
| 2010/0114095 A1 | 5/2010 | Janssen et al. |
| 2010/0143413 A1 | 6/2010 | Papay |
| 2010/0145221 A1 | 6/2010 | Brunnett et al. |
| 2010/0286554 A1 | 11/2010 | Davis et al. |
| 2011/0028860 A1 | 2/2011 | Chenaux et al. |
| 2011/0034826 A1 | 2/2011 | Notz et al. |
| 2011/0237974 A1 | 9/2011 | Bartol et al. |
| 2013/0331835 A1 | 12/2013 | Leung et al. |

OTHER PUBLICATIONS

Ristićet al., "Analgesic and antinociceptive effects of peripheral nerve neurostimulation in an advance human experimental model", European Journal of Pain, vol. 12, No. 4, Mar. 4, 2008, pp. 480-490.
International Search Report and Written Opinion for PCT/US2015/046485, dated Jan. 18, 2016, 20 pages.

\* cited by examiner

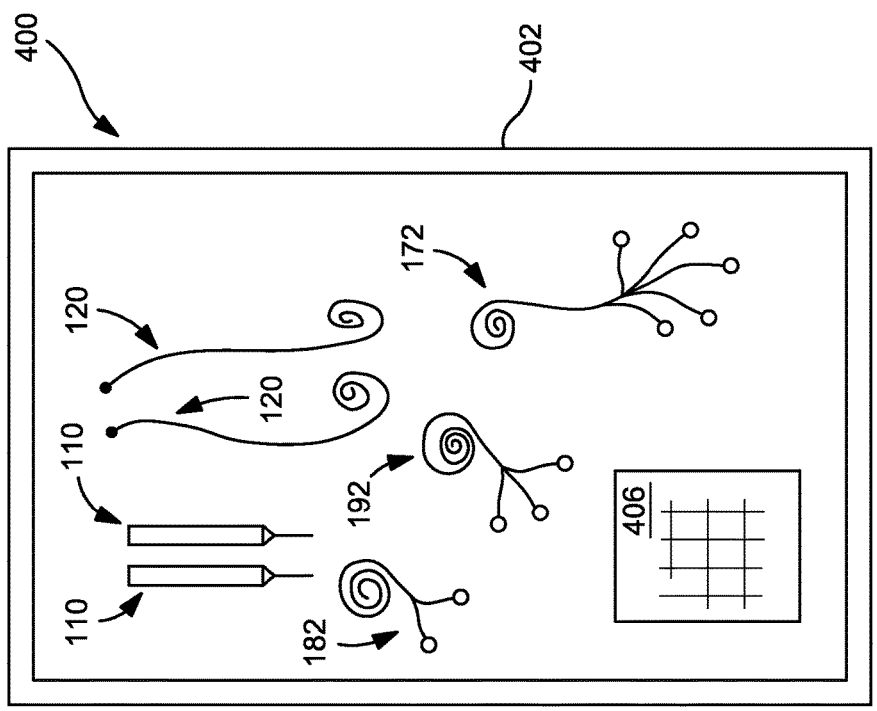

METHOD AND SYSTEM FOR IDENTIFICATION OF SOURCE OF CHRONIC PAIN AND TREATMENT

RELATED APPLICATIONS

This application is the national stage entry of International Patent Application No. PCT/US2015/046485 having a filing date of Aug. 24, 2015, which claims priority to U.S. Provisional Application No. 62/041,798, filed on Aug. 26, 2014, both of which are incorporated herein in their entirety by reference thereto.

BACKGROUND OF THE INVENTION

It is estimated that as many as 70 million Americans experience chronic pain, and a worldwide study has concluded that between 10% and 55% of the population experiences chronic pain. In contrast to acute pain, which is associated with an inflammatory response in the early stages of healing, the International Association for the Study of Pain defines chronic pain as pain that persists past the normal time of healing or past the healing phase following an injury, as discussed in Bonica, J. J., "The Management of Pain," Lea & Febiger, Philadelphia, 1953 and Merskey, et al., "Classification of Chronic Pain Syndromes and Definitions of Pain Terms," Second Edition, 1994, which are incorporated herein by reference. Examples of chronic pain include lower back pain, migraine, fibromyalgia, complex regional pain syndrome, cancer pain, and spinal cord injury pain, to name a few.

The mechanisms responsible for chronic pain are largely unknown, and its treatments are often unsuccessful. The technique of nerve ablation is a destructive method of treating chronic pain by interrupting the transmission of neural signals that contribute to painful circuitry. The technique requires a physician to pass a probe percutaneously into the vicinity of nerve suspected of causing chronic pain, and deliver ablative energy through the probe to the nerve.

Physicians have expressed a need, which has thus far been unmet, for an embodiment and quantitative method to direct the ablative probe to the nerve that contributes to the painful circuitry, to interrogate the nerve for its role in chronic pain, to treat the nerve without removing the probe, to immediately confirm that the nerve has been lesioned and is no longer viable, and to confirm that the lesion has successfully disrupted the chronic pain circuitry. The challenge in enabling a solution is inherent to the pain type. Unlike acute pain, or nociceptive pain, chronic pain is governed by plastic changes in the spinal cord, brain, and the periphery. The neuroplastic changes responsible for chronic pain may include augmentation or modification of existing circuitry, aberrant neural circuitry and/or changes enabled by non-neural structures. The most predictive markers of chronic pain are brain derived, and include: (1) Brain chemistry; (2) Cognition; (3) Brain morphometry; (4) Spontaneous fluctuations of pain; and (5) Brain activity.

In "Towards a theory of chronic pain", Progress in Neurobiology, Vol. 87, No. 2, February 2009, pages 81-97, A. Vania Apkarian, Marwan N. Baliki, and Paul Y. Geha, the authors used functional magnetic resonance imaging (fMRI) to discern brain regions that where active in persons with chronic back pain. Accordingly, they found neural activation patterns in regions of the brain (medial prefrontal cortex) that are atypical of ordinary pain. The authors suggest that the activity and site can be used to mark chronic back pain. Despite fMRI's abilities to discern markers of chronic pain in humans, the technology itself is poorly suited for the clinical setting. Functional magnetic imaging technologies are expensive, take up valuable room space, require a controlled operating environment (i.e., non-ferromagnetic tools) and are unable to provide timely acquisition and analysis of recorded data (poor temporal resolution).

As such, there is an unmet need for a system or apparatus for identifying or locating a source of or neural pathway associated with chronic pain, as well as for treating the chronic pain once its source has been identified. There is also a need for a practical and effective method for identifying or locating a source of chronic pain or a neural pathway associated with chronic pain, as well as for treating the chronic pain once its source has been identified.

SUMMARY OF THE INVENTION

In accordance with one embodiment of the present invention, a method for identifying a neural pathway associated with chronic pain via nerve stimulation and brain wave monitoring of a mammalian brain is disclosed. The method includes positioning a probe to stimulate a target nerve, wherein the target nerve is suspected of being a source of chronic pain; delivering a first nerve stimulation from the probe to the target nerve, wherein the first nerve stimulation is sufficient to elicit a chronic pain response in the brain; and monitoring for potential activity in the brain as a result of the first nerve stimulation.

In one embodiment, the method can include monitoring for evoked potential activity in one or more predetermined regions of the brain, wherein the presence of evoked potential activity in the one or more predetermined regions of the brain can indicate that the target nerve is part of the neural pathway associated with chronic pain.

In another embodiment, monitoring for evoked potential activity can include measuring evoked potential amplitude, wherein an increase in evoked potential amplitude can indicate that the probe is positioned closer to the source of the chronic pain and a decrease in evoked potential amplitude can indicate that the probe is positioned farther away from the source of the chronic pain. Further, with such monitoring, the first nerve stimulation can be delivered at a constant waveform, pulse duration, frequency, intensity, or a combination thereof.

In still another embodiment, monitoring for evoked potential activity can include measuring evoked potential latency, wherein a decrease in evoked potential latency can indicate that the probe is positioned closer to the source of the chronic pain and an increase in evoked potential latency can indicate that the probe is positioned farther away from the source of the chronic pain. Further, with such monitoring, the first nerve stimulation can be delivered at a constant waveform, pulse duration, frequency, intensity, or a combination thereof.

In one more embodiment, monitoring for evoked potential activity can include measuring evoked potential frequency, wherein an increase in evoked potential frequency can indicate that the probe is positioned closer to the source of the chronic pain and a decrease in evoked potential frequency can indicate that the probe is positioned farther away from the source of the chronic pain. Further, with such monitoring, the first nerve stimulation can be delivered at a constant waveform, pulse duration, frequency, intensity, or a combination thereof.

In yet another embodiment, the method can include monitoring for evoked potential activity in one or more predetermined regions of the brain, wherein the presence of evoked potential activity with a predetermined amplitude, a predetermined latency, a predetermined frequency, a predetermined shape, or a combination thereof in the one or more predetermined regions of the brain can indicate that the target nerve is part of the neural pathway associated with chronic pain.

In an additional embodiment, monitoring for evoked potential activity can include measuring evoked potential amplitude, evoked potential latency, evoked potential frequency, evoked potential shape, or a combination thereof, wherein observation of an evoked potential with sufficient amplitude, latency, frequency, shape, or a combination thereof at a predetermined stimulation can indicate that the target nerve is in close enough proximity to the part of the neural pathway associated with the chronic pain for treatment of the chronic pain.

Further, the method can include delivering a second nerve stimulation from the probe at a location along the target nerve where the evoked potential activity with sufficient amplitude, latency, frequency, shape, or a combination thereof is observed, wherein the second nerve stimulation is sufficient to create a nerve block; monitoring brain wave activity as the second nerve stimulation is delivered; confirming the target nerve has been correctly identified as part of the neural pathway associated with chronic pain if brain wave activity consistent with an effective nerve block is observed during application of the nerve block; and determining that the target nerve is not a part of the neural pathway associated with chronic pain if brain wave activity inconsistent with an effective nerve block is observed during the nerve block.

In addition, the method can include treating the chronic pain when the target nerve is correctly identified as part of the neural pathway associated with chronic pain, wherein treating the chronic pain can include delivering a third nerve stimulation from the probe at the location along the target nerve where the evoked potential activity with sufficient amplitude, latency, frequency, shape, or a combination thereof is observed, wherein the third nerve stimulation can be sufficient to impair the neural pathway associated with the chronic pain.

Moreover, the method can include verifying impairment of the neural pathway is complete by repeating the first nerve stimulation, the second nerve stimulation, or both to confirm effective impairment of the target nerve, wherein impairment is complete if brain wave activity consistent with effective impairment of the neural pathway is observed.

Further, the method can include delivering an additional nerve stimulation to an additional nerve via the probe, wherein the additional nerve is not suspected of being a source of chronic pain, wherein the additional nerve stimulation is sufficient to elicit a response in the brain; and monitoring for baseline activity in the brain, evoked potential activity in the brain as a result of the additional nerve stimulation, or both via the electroencephalography electrodes. Further, the method can also include comparing the elicited response from the additional nerve stimulation to the elicited response from the first nerve stimulation to verify that the target nerve is correctly identified as part of the neural pathway associated with chronic pain, wherein a difference in the elicited response from the additional nerve stimulation compared to the elicited response from the first nerve stimulation indicates that the target nerve is part of the neural pathway associated with chronic pain.

In one embodiment, monitoring for evoked potential activity is performed via electroencephalography. In another embodiment, the probe used to carry out the method can be a percutaneous probe. In an additional embodiment, the first nerve stimulation can be electrical. Similarly, in other embodiments, the second nerve stimulation, the third nerve stimulation, and the additional (fourth) nerve stimulation can be electrical. The first nerve stimulation can be delivered at a frequency of less than about 100 Hertz and at an amplitude ranging from about 0.01 milliamps to about 50 milliamps. Further, the first nerve stimulation can be delivered as a square wave, wherein each pulse of the square wave has a duration ranging from about 0.01 milliseconds to about 10 milliseconds. Meanwhile, the second nerve stimulation can be delivered at a frequency ranging from about 1,000 Hertz to about 100,000 Hertz and at an amplitude ranging from about 0.01 milliamps to about 50 milliamps. Further, the third nerve stimulation can be delivered at a frequency ranging from about 200,000 Hertz to about 1 Megahertz and at an amplitude of up to about 1.4 Amps.

In yet another embodiment, a system for identifying a neural pathway associated with chronic pain via nerve stimulation and brain wave monitoring is disclosed. The system includes a probe; electroencephalography electrodes; and a controller coupled to the probe and the electroencephalography electrodes. The controller is configured to deliver a first nerve stimulation to a target nerve via the probe, wherein the target nerve is suspected of being a source of chronic pain, wherein the first nerve stimulation is sufficient to elicit a chronic pain response in the brain. In addition, the controller is configured to monitor for baseline activity in the brain, evoked potential activity in the brain as a result of the first nerve stimulation, or both via the electroencephalography electrodes.

In one particular embodiment, the system can monitor for evoked potential activity in one or more predetermined regions of the brain, wherein the presence of evoked potential activity in the one or more predetermined regions of the brain can indicate that the target nerve is part of the neural pathway associated with chronic pain.

In another embodiment, the system can monitor for evoked potential activity by measuring evoked potential amplitude, wherein an increase in evoked potential amplitude can indicate that the probe is positioned closer to the source of the chronic pain and a decrease in evoked potential amplitude can indicate that the probe is positioned farther away from the source of the chronic pain. Further, with such monitoring, the first nerve stimulation can be delivered at a constant waveform, pulse duration, frequency, intensity, or a combination thereof.

In one more embodiment, the system can monitor for evoked potential activity by measuring evoked potential latency, wherein a decrease in evoked potential latency can indicate that the probe is positioned closer to the source of the chronic pain and an increase in evoked potential latency can indicate that the probe is positioned farther away from the source of the chronic pain. Further, with such monitoring, the first nerve stimulation can be delivered at a constant waveform, pulse duration, frequency, intensity, or a combination thereof.

In yet another embodiment, the system can monitor for evoked potential activity by measuring evoked potential frequency, wherein an increase in evoked potential frequency can indicate that the probe is positioned closer to the source of the chronic pain and a decrease in evoked potential frequency can indicate that the probe is positioned farther away from the source of the chronic pain. Further, with such monitoring, the first nerve stimulation can be delivered at a constant waveform, pulse duration, frequency, intensity, or a combination thereof.

In still another embodiment, the system can monitor for evoked potential activity in one or more predetermined regions of the brain, wherein the presence of evoked potential activity with a predetermined amplitude, a predetermined latency, a predetermined frequency, a predetermined shape, or a combination thereof in one or more predetermined regions of the brain can indicate that the target nerve is part of the neural pathway associated with chronic pain.

In an additional embodiment, the system can monitor for evoked potential activity by measuring evoked potential amplitude, evoked potential latency, evoked potential frequency, evoked potential shape, or a combination thereof, wherein observation of an evoked potential with sufficient amplitude, latency, frequency, shape, or a combination thereof at a predetermined stimulation can indicate that the target nerve is in close enough proximity to a part of the neural pathway associated with chronic pain for treatment of the chronic pain.

Further, the system's controller can be configured to deliver a second nerve stimulation via the probe delivering a second nerve stimulation from the probe at a location along the target nerve where the evoked potential activity with sufficient amplitude, latency, frequency, shape, or a combination thereof is observed, wherein the second nerve stimulation is sufficient to create a nerve block; monitor brain wave activity as the second nerve stimulation is delivered, further wherein the system; confirm the target nerve has been correctly identified as part of the neural pathway associated with chronic pain if brain wave activity consistent with an effective nerve block is observed during application of the nerve block; and determine that the target nerve is not a part of the neural pathway associated with chronic pain if brain wave activity inconsistent with an effective nerve block is observed during the nerve block.

In an additional embodiment, the system can treat chronic pain when the target nerve is correctly identified as part of the neural pathway associated with chronic pain, wherein the controller can be configured to deliver a third nerve stimulation from the probe at the location along the target nerve where the evoked potential activity with sufficient amplitude, latency, frequency, shape, or a combination thereof is observed, wherein the third nerve stimulation can be sufficient to impair the neural pathway associated with the chronic pain.

Moreover, the controller can be further configured to verify impairment of the neural pathway is complete by repeating the first nerve stimulation, the second nerve stimulation, or both to confirm effective impairment of the target nerve, wherein impairment is complete if brain wave activity consistent with effective impairment of the neural pathway is observed.

In still another embodiment, the controller can be configured to deliver an additional nerve stimulation to an additional nerve via the probe, wherein the additional nerve is not suspected of being a source of chronic pain, wherein the additional nerve stimulation is sufficient to elicit a response in the brain, further wherein the controller is configured to monitor for baseline activity in the brain, evoked potential activity in the brain as a result of the additional nerve stimulation, or both via the electroencephalography electrodes. Further, the elicited response from the additional nerve stimulation can be compared to the elicited response from the first nerve stimulation to verify that the target nerve is correctly identified as part of the neural pathway associated with chronic pain, wherein a difference in the elicited response from the additional nerve stimulation compared to the elicited response from the first nerve stimulation indicates that the target nerve is part of the neural pathway associated with chronic pain.

In the system of the present invention, the probe can be a percutaneous probe. In an additional embodiment, the first nerve stimulation can be electrical. Similarly, in other embodiments, the second nerve stimulation, the third nerve stimulation, and additional (fourth) stimulation can be electrical. The first nerve stimulation can be delivered at a frequency of less than about 100 Hertz and at an amplitude ranging from about 0.01 milliamps to about 50 milliamps. Meanwhile, the second nerve stimulation can be delivered at a frequency ranging from about 1,000 Hertz to about 100,000 Hertz and at an amplitude ranging from about 0.01 milliamps to about 50 milliamps. Further, the third nerve stimulation can be delivered at a frequency ranging from about 200,000 Hertz to about 1 Megahertz and at an amplitude of up to about 1.4 Amps. In an additional embodiment, the controller can transmit the first nerve stimulation to the probe via a pulse generator connected to the probe via an electrical lead. In still another embodiment, the controller can transmit the second nerve stimulation to the probe via a pulse generator connected to the probe via an electrical lead. In yet another embodiment, the controller can transmit the third nerve stimulation to the probe via a pulse generator connected to the probe via an electrical lead.

In an additional embodiment, an apparatus for treating chronic pain is disclosed. The apparatus includes at least one probe for delivering multiple nerve stimulations, wherein a first nerve stimulation identifies a source of chronic pain, a second nerve stimulation verifies the source of chronic pain has been identified, and a third nerve stimulation treats the chronic pain; and a monitor configured to display multiple views.

In another embodiment, the apparatus can include at least one probe. In still another embodiment, the apparatus can include multiple RF probes. In another embodiment, the apparatus can be configured to have multiple channels, wherein each channel is configured to treat a different source or location of chronic pain.

In another embodiment, the monitor can include a display screen having multiple views. Further, the display screen can have a first view, a second view, and a third view, wherein the first view displays information related to identifying a source of chronic pain, the second view displays information related to verifying the source of chronic pain, and the third view displays information related to treating chronic pain.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 4(*b*) is a graph showing multiple evoked potentials elicited by a single stimulation (vertical dashed line). Plot A shows an evoked potential that is elicited with a latency of $\Delta t_0$, where the evoked potential then reoccurs at regular intervals ($\Delta t_1 = \Delta t_2 = \Delta t_3$). Plot B shows a phenomenon called wind-up, where the stimulation elicits re-occurring evoked potentials that increase in frequency with each occurrence.

FIG. 4(*c*) is a graph describing evoked potential activity recorded before (Plot A) and after (Plot B) nerve ablation or high-frequency nerve blocking. An evoked potential is demonstrated in Plot A following stimulation (vertical dashed line) and is not present in Plot B.

FIG. 5 is a top view of an exemplary kit that may be used in the diagnosis and treatment of chronic pain.

Figure 1:
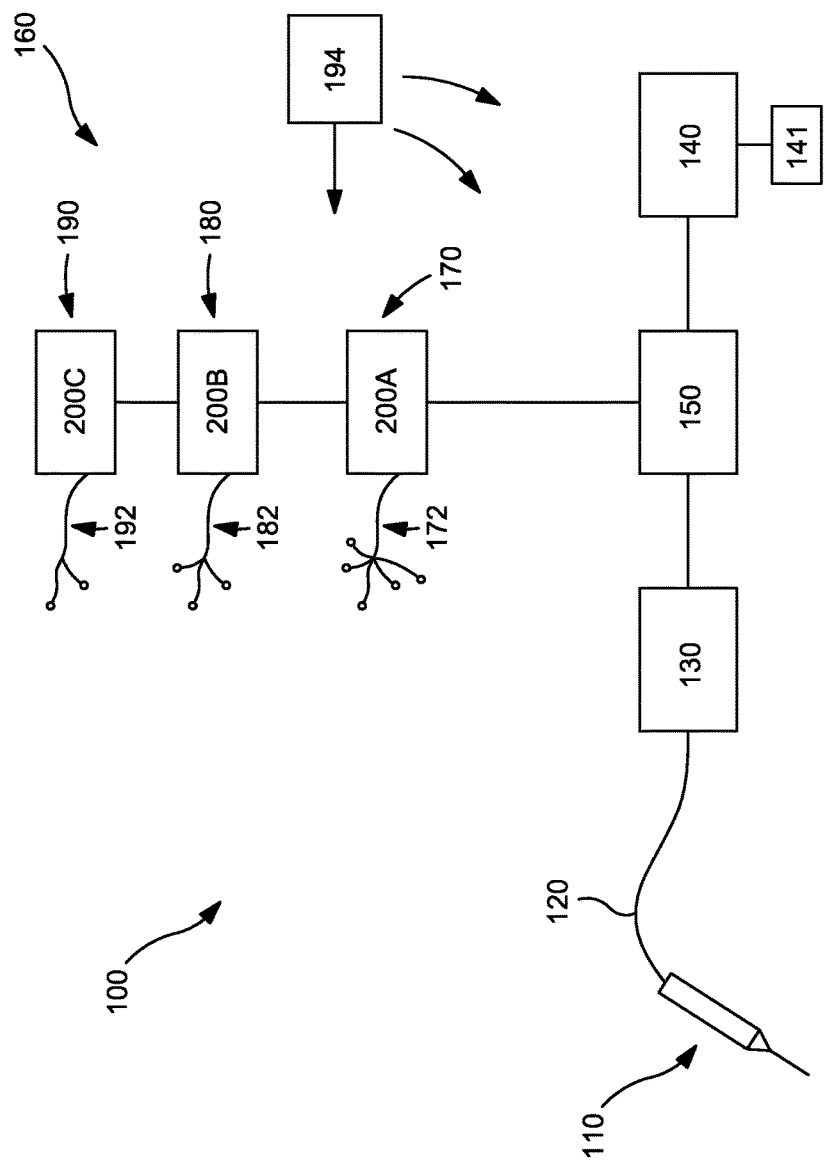
FIG. 1 is schematic diagram of an exemplary system for diagnosing and treating chronic pain.

Repeat use of reference characters in the present specification and drawings is intended to represent same or analogous features or elements of the invention.

DEFINITIONS

As used herein, the term "brain wave monitoring" refers to the observation of neural or neurological activity in the brain that can be baseline, spontaneous, or elicited. Observation can be through electrodes via electroencephalography (EEG) or any other suitable means. In other words, brain wave monitoring refers to observation of electrical potential in the brain as represented on an electroencephalogram.

As used herein, the term "evoked potential" refers to an outcome measure of neurological activity in response to nerve stimulation. For example, an evoked potential may refer to a burst of neurological activity in response to a nerve stimulation.

As used herein, the term "low frequency electrical nerve stimulation" refers to the application of low frequency electrical energy in a waveform that elicits an evoked potential (EP). As a non-limiting example, the frequency at which the low frequency electrical nerve stimulation is delivered can be about 100 Hertz (Hz) or less.

As used herein, the term "high frequency electrical nerve blocking stimulation" refers to the application of high frequency electrical energy in a waveform that blocks the propagation of action potentials through the stimulation or block site. As a non-limiting example, the frequency at which the high frequency electrical nerve stimulation is delivered can range from about 1,000 Hz to about 100,000 Hz.

As used herein, the term "nerve ablation" refers to the creation of a lesion on a nerve to interrupt the transmission of pain signals to the brain using ultra-high frequency stimulation (e.g., with alternating-current). Nerve ablation can provide long-term relief from pain associated with the nerve on which the ablation is performed.

As used herein, the term "nerve impairment" refers to any disruption, alteration, destruction, lesioning, or ablation of a nerve or neural pathway such that neurological (e.g., pain) signals originating at or around the nerve or neural pathway do not transmit through the impaired site.

As used herein, the term "nerve block" refers to a reversibly or temporary interrupting, hindering, or preventing of the passage of impulses along a neuron's axon. The term can also encompass a form of regional anesthesia in which insensibility is produced in a part of the body by temporarily interrupting, hindering, or preventing of the passage of impulses along a neuron's axon, making the nerve inoperable.

As used herein, the term "neural pathway" refers to a means of connecting one part of the nervous system with another.

As used herein, the term "nerve stimulation" refers to any means of stimulating a nerve, such as, but not limited to, electrical stimulation, mechanical stimulation, thermal stimulation (including but not limited to the application of cryogenic energy), or chemical stimulation.

As used herein, the term "ultra-high electrical nerve stimulation" refers to the application of ultra-high frequency electrical energy in a waveform that sufficiently impairs a nerve to prevent or inhibit the propagation of evoked potentials through the stimulation site. As a non-limiting example, the frequency at which the ultra-high frequency electrical nerve stimulation is delivered can be greater than about 100,000 Hz.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a system and method for identifying a neural pathway associated with chronic pain via nerve stimulation and brain wave monitoring. It is to be understood that the system and method can identify sources of chronic pain as distinguished from acute pain, as chronic pain is observed in different areas of the brain and with different activation patterns as compared to acute pain. Neurological markers (e.g., aberrant neural activity) of chronic back pain have been recorded from the medial prefrontal cortex and dorsolateral prefrontal cortex of the human brain. Allodynia pain in post herpetic neuralgia patients is marked by activity in the insula cortex, S2, and basal ganglia. Similarly, pain in persons with osteoarthritis is marked mainly by the insula cortex. The system and method of the present invention identifies the neural pathway responsible for the chronic pain via a first stimulation of a target nerve, and can then verify that the correct target nerve has been identified via a second stimulation of the target nerve. Thereafter, the chronic pain can be treated via a third stimulation of the target nerve. In addition, an additional nerve not associated with chronic pain can be stimulated via an additional (fourth stimulation), and the resulting elicited response can be used as a reference response to provide additional verification that the target nerve is the source of the chronic pain, as an elicited response from a nerve associated with chronic pain will have different characteristics than an elicited response from a healthy nerve.

To carry out a first stimulation of one or more target nerves of interest, a probe can be positioned in a desired location to stimulate the target nerve, where the target nerve being stimulated is suspected of being a source of chronic pain. Then a first nerve stimulation can be delivered from the probe to the target nerve where the stimulation is sufficient to elicit a chronic pain response in the brain, and evoked potential activity in the brain as a result of the first nerve stimulation can be monitored. For instance, the stimulation can be delivered at a high enough intensity (e.g., current) or voltage such that a chronic pain response is elicited.

In various embodiments, different types of monitoring can be carried out to identify the neural pathway associated with chronic pain. In one particular embodiment, evoked potential activity in one or more predetermined regions of the brain can be monitored, and the presence of evoked potential activity in the one or more predetermined regions of the brain can indicate that the target nerve being stimulated at the point is a part of the neural pathway associated with the chronic pain.

In another embodiment, the first nerve stimulation can be delivered and, at the same time, evoked potential amplitudes in an area of the brain can be measured. Further, the first nerve stimulation can be delivered at a constant waveform, pulse duration, frequency, intensity, or a combination thereof as the probe is moved near an area that is suspected of being the source of chronic pain. With such monitoring, an increase in evoked potential amplitude can indicate that the probe is positioned closer to the source of the chronic pain when comparing an evoked potential measurement to previous evoked potential amplitude measurements. Meanwhile, a decrease in evoked potential amplitude can indicate that the probe is positioned farther away from the source of the chronic pain when comparing an evoked potential amplitude measurement to previous evoked potential amplitude measurements.

In another embodiment, the first nerve stimulation can be delivered and the latency between resulting evoked potentials can be measured. It should be understood that in such an embodiment, the first nerve stimulation can be delivered at a constant waveform, pulse duration, frequency, intensity, or a combination thereof as the probe is moved near an area that is suspected of being the source of chronic pain. With such monitoring, a decrease in the latency between evoked potentials can indicate that the probe is positioned closer to the source of the chronic pain when comparing the time between two evoked potentials to the time between previously measured evoked potentials. Meanwhile, an increase in the latency between evoked potentials can indicate that the probe is positioned farther away from the source of the chronic pain when comparing the time between two evoked potentials to the time between previously measured evoked potentials. Meanwhile, the frequency between resulting evoked potentials as a result of a first nerve stimulation can also be measured, where an increase in the frequency of measured evoked potentials over time can indicate that the probe is positioned closer to the source of the chronic pain, while a decrease in the frequency of measured evoked potentials over time can indicate that the probe is positioned farther away from the source of the chronic pain when comparing the number of evoked potentials measured per unit of time.

In still another embodiment, monitoring during the first nerve stimulation can include monitoring for evoked potential activity in or more predetermined regions of the brain, such as but not limited to the medial prefrontal cortex, dorsolateral prefrontal cortex, insular cortex, or any other area of the brain where chronic pain can present itself. If evoked potential activity having a predetermined amplitude, a predetermined latency, a predetermined frequency, a predetermined shape, or a combination thereof as determined via a chronic pain algorithm, or study, is present in one or more predetermined regions of the brain, then it can be concluded that the target nerve being stimulated is part of the neural pathway associated with chronic pain. Further, the region of the brain in which the evoked potential activity is present can be used to determine the particular type or types of chronic pain being experienced.

In yet another embodiment, monitoring during the first nerve stimulation can include measuring evoked potential amplitude, latency, frequency, shape, or a combination thereof at or during a predetermined stimulation means, level, cycle, or parameter. In such an embodiment, observation of an evoked potential with sufficient amplitude, latency, frequency, shape, or a combination thereof at the predetermined stimulation means, level, cycle, or parameter can indicate that the target nerve is in close enough proximity to a part of the neural pathway associated with chronic pain so that the chronic pain can be treated using the system and method of the present invention.

Once a target nerve has been identified as part of the neural pathway associated with chronic pain, then a second nerve stimulation can be delivered from the probe, such as at a location along the target nerve where the evoked potential activity with sufficient amplitude, latency, frequency, shape, or a combination thereof was observed to indicate that a chronic pain response was elicited. The second nerve stimulation can be sufficient to create a nerve block. Further, brain wave activity can be monitored during delivery of the second nerve stimulation, and it can be confirmed that the target nerve has been correctly identified as part of the neural pathway associated with chronic pain if brain wave activity consistent with an effective nerve block is observed during application of the nerve block (e.g., minimal or no evoked potential activity is observed). Meanwhile, it can be confirmed that the target nerve is not a part of the neural pathway associated with chronic pain if brain wave activity inconsistent with an effective block is observed during the nerve block (e.g., significant evoked potential activity is observed).

After identifying a target nerve is part of the neural pathway associated with chronic pain, and optionally after verification that the target nerve has been correctly identified via nerve block, the chronic pain can be treated via a third nerve stimulation. For instance, the third nerve stimulation can be delivered from the probe at a location along with target nerve where the evoked potential activity with sufficient amplitude, latency, frequency, shape, or a combination thereof is observed, where the third nerve stimulation is sufficient to impair the neural pathway associated with the chronic pain. Thereafter, the first nerve stimulation, second nerve stimulation, or both can be repeated to confirm or verify effective impairment of the target nerve, where impairment is complete or sufficient if brain wave activity consistent with effective impairment of the neural pathway is observed (e.g., minimal or no evoked potential activity is observed).

In another embodiment, an additional (fourth) nerve stimulation can be delivered from the probe at a location along an additional nerve other than the target nerve, where the additional nerve is not suspected of being a source of chronic pain, and the resulting. The resulting elicited response or evoked potential activity can be compared with the elicited response from the first nerve stimulation of the target nerve. For instance, the amplitude, latency, frequency, shape, or a combination thereof exhibited by the elicited response resulting from the stimulation of the additional nerve can serve as a reference for how an elicited response or evoked potential from a healthy nerve appears, which can be used as verification that the target nerve is part of the neural pathway associated with chronic pain if the elicited response or evoked potential of the target nerve is distinct or different in appearance as compared to the elicited response or evoked potential of the additional nerve.

The particular type of nerve stimulations described above can vary, such as electrical, mechanical, chemical, etc. Regardless of the type of nerve stimulation delivered, it is to be understood that the nerve stimulation can be delivered via a probe such as a percutaneous probe, or by any other suitable means. In addition to the probe, the system of the present invention can include an electroencephalography (EEG) monitor, and EEG electrodes. In one particular embodiment, the system can further include a pulse generator electrically attached to the probe to deliver a first (low frequency) electrical nerve stimulation to the nerve, at which time the evoked potentials (EPs) in the area of the brain associated with the nerve stimulation can be observed via EEG as a means to identify the particular nerve associated with the chronic pain. Thereafter, the pulse generator can deliver a second (high frequency) electrical nerve stimulation to the target nerve that serves as a nerve block. If the EPs on the EEG are silenced as a result of the second (high frequency) electrical nerve stimulation, a user can have verification that the target nerve is associated with the neural pathway responsible for the chronic pain (i.e., the chronic pain source) and can then impair the nerve or neural pathway via a third (ultra-high frequency) electrical nerve stimulation, such as by ablation to form a lesion, or by any other suitable method, to sufficiently modify or destroy the pain pathway responsible for the chronic pain such that the pain is no longer felt. Successful impairment/ablation can then be verified via repeating the first (low frequency) electrical nerve stimulation at the impairment/ablation site, the second (high frequency) electrical nerve stimulation at the ablation site, or both, to confirm effective impairment of the target nerve, where impairment is complete if brain wave activity consistent with effective impairment of the neural pathway is observed. For instance, if EPs in the brain as measured via EEG are silenced, a user can have verification that the nerve causing a patient's chronic pain has been sufficiently impaired or ablated such that the patient no longer feels the chronic pain. Although one particular embodiment includes electrical nerve stimulation via a pulse generator as discussed above, it is also to be understood that the nerve stimulation can be carried out by mechanical, chemical, or other suitable means using a probe or other delivery device. In this regard, various embodiments of the present invention will now be discussed in more detail below.

Referring now to FIG. 1 of the drawings, there is illustrated a chronic pain management system that can locate a target nerve and/or identify a neural pathway associated with or responsible for chronic pain via a first (low frequency) electrical nerve stimulation, can deliver a second (high frequency) electrical nerve-blocking stimulation to the target nerve to verify that the target nerve is the source of the chronic pain, can deliver a third (ultra-high frequency) electrical nerve stimulation to ablate or otherwise sufficiently impair the target nerve, and can repeat either the first (low frequency) electrical nerve stimulation, the second (high frequency) electrical nerve stimulation, or both to ensure that the target nerve has been successfully ablated. The system can deliver an additional (fourth) electrical nerve stimulation to an additional nerve so that the resulting elicited response can be used as a reference for verification that the target nerve is part of the neural pathway associated with chronic pain as discussed above. Generally, the electrical nerve stimulation(s) may be delivered to the target nerve utilizing a percutaneous probe. The chronic pain management system includes multiple devices to control and deliver predetermined electrical pulses at predetermined voltages, frequencies, amplitudes (currents), etc. to one or more target nerve(s). As shown in FIG. 1, the chronic pain management system 100 includes a probe 110 that is connected by an electrical lead 120 to the rest of the system 100—which includes a pulse generator 130, a user interface 140, a display 141, and a controller 150. The probe can be a percutaneous probe 110 or any other suitable probe. The system also includes a patient monitor system 160, and may further include an isolated power system 180. Each component is discussed in more detail below.

PROBE

Figure 2:
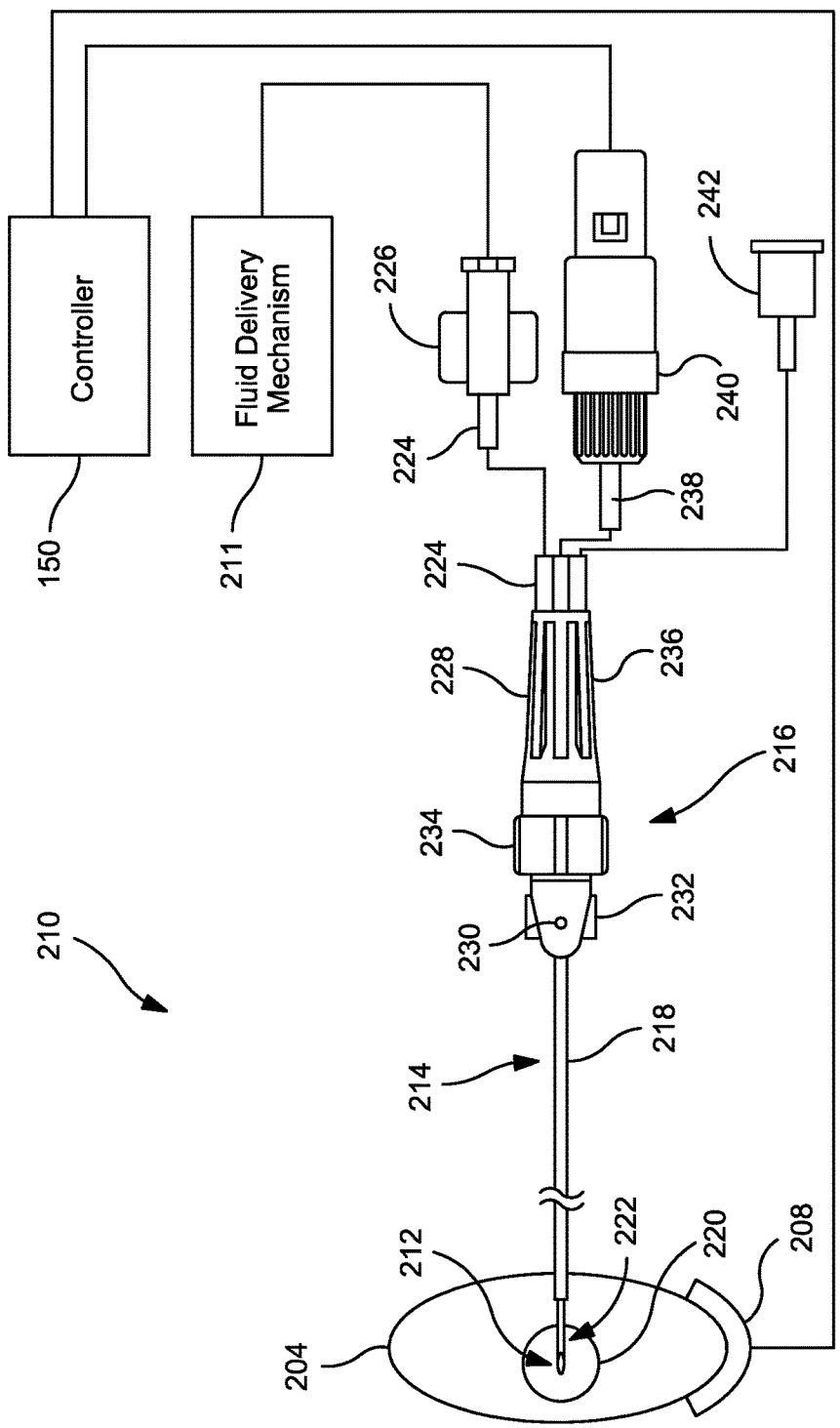
FIG. 2 is a perspective side view of an exemplary probe utilized for stimulating a nerve, delivering electrical energy directly to the vicinity of a target nerve to block nerve fiber activity, and ablating the nerve.

While any suitable probe 110 can be utilized in the chronic pain management system 100 of the present invention, FIG. 2 shows one example of a suitable percutaneous probe 210 in more detail. Referring to FIG. 2, a probe 210 that can be used in a system 100 (see FIG. 1) for stimulating a target nerve 220 is shown. The probe 210 can be coupled to a controller 150 that, among other things, regulates a pulse generator 130 (see FIG. 1), and may also include a return dispersive electrode 208 and a fluid delivery mechanism 210, such as, but not limited to, a syringe, for fluid composition injection. The pulse generator 130 may be controlled to supply energy, such as radiofrequency (RF) energy, to the probe 210, while the controller 150 can also measure temperature feedback from at least one temperature sensor of probe 210. Further, impedance measurement can be carried out between a conductive region 212 of the probe 210 and the return dispersive electrode 208. Impedance measurement may be used during placement of the probe to locate an area of nerve tissue that has specific electrical properties. In addition, the controller 150 may respond to evoked potentials (EP) as determined by electroencephalography (EEG), electrocardiogram (ECG) measurements, electromyogram (EMG) measurements, or other means for evaluating a patient's response to a treatment procedure, as discussed in more detail below.

The probe 210 may comprise a conductive shaft 214 and a handle 216. Conductive shaft 214 can have an insulating coating 218 along a major portion of its outer surface, terminating adjacent exposed conductive region 212. A conductive region 212 can be operable to transmit energy to a target nerve 220 of a neural pathway 204. In addition, the conductive region 212 may aid in the penetration of the probe 210 into, near or around a neural pathway 204 and in the navigation of the probe 210 to a desired target nerve 220. It will therefore be understood by a person skilled in the art that the conductive region 212 can be of varying dimensions and shapes and may be positioned at various locations on a probe 210 utilized in the present invention. For example, the conductive region 212 can be pointed, sharp, blunt, or open, varying in shape in accordance with the requirements of different procedures. Also, while the length of the conductive region 212 in the first embodiment is between about 2 mm to about 10 mm, this length can vary depending on procedural requirements. The conductive region 212 can optionally be made of medical grade stainless steel, but other conductive biocompatible materials can be used as well.

In one embodiment, the shaft 214 and conductive region 212 can be made from a conductive material, for example, stainless steel. Meanwhile, the insulating coating 218 can be made of any type of insulating material, including, but not limited to, polyethylene terephthalate (PET), to prevent the shaft 214 from delivering high frequency electrical current to tissue surrounding the shaft 214. Further, the shaft 214 can have at least one aperture 222 in some embodiments, through which a treatment composition can be administered and exit from the probe 210.

The conductive shaft 214 of the probe 210 may impart rigidity to the probe 210 to facilitate the maneuvering of the conductive region 212 to reach a target nerve 220 of a neural pathway 204, in which case the shaft 214 may be referred to as being rigid or semi-rigid. In other embodiments, the shaft 214 can be flexible. In one embodiment, the shaft 214 can be hollow along its length, defining a lumen. The shaft 214 can be used to transmit a treatment composition to the conductive region 212 and/or the target nerve 220, as well as to support and enclose any wiring associated with the probe 210. Further, an inner diameter of the shaft 214 can be sufficiently dimensioned to accommodate a stylet or obturator in embodiments with an open tip, in addition to wiring for a temperature sensor associated with the distal end of the shaft 214. In some embodiments, the length of the shaft 214 can vary between about 5 cm to about 15 centimeters. It is understood, however, that the length can vary beyond this range according to the location of the target nerve and/or the procedure being performed.

In one embodiment, the handle 216 can include a flexible tube 224 coupled thereto in fluid communication with the lumen of the shaft 214. The flexibility of the tube 224 can allow for greater maneuverability of the probe 210. A proximal end of the flexible tube 224 can be coupled to a fluid delivery interface connection 226. In other embodiments (not shown), the handle 216 may not be necessary and the flexible tube 224 can be coupled directly to shaft 214. The handle 216 can optionally provide a grip 228 to allow a user to more easily manipulate the probe 210. In one embodiment, the handle 216 is manufactured from medical grade injection-moldable plastic or other material that can be sterilized using, for example, ethylene oxide. The handle 216 can also have an aperture marker 230 that is in line with an aperture 222 along the axis of the shaft 214 and which can be used to indicate the orientation of the aperture 222 about the axis of the shaft 214. An aperture marker 230 allows the user to target tissue for the delivery of a treatment composition by indicating the orientation of the aperture 222. The handle 216 can further comprise orientation markings, including first orientation markings 232 to indicate, for example, 180° rotation of the probe 210 about the axis of the shaft 214 and second orientation markings 234 to indicate, for example, 90° rotation of the probe 210 about the axis of the shaft 214. The user can then refer to first and/or second orientation markings 232, 234 to prevent the probe 210 from rotating about the axis of the shaft 214 while the probe 210 is inserted through nerve tissue at or near neural pathway 204, or to rotate the probe 210 about the axis of the shaft 214 to a desired orientation. The first and second orientation markings 232, 234 can be visual indicators, which can be flush with the handle 216, or tactile indicators, which can be textured or raised so that the user can see or feel the markings 232, 234 as the probe 210 is inserted into nerve tissue at or near a neural pathway 204. A proximal end of the handle 216 can also have a strain relief 236 with a grip 228 running from the proximal end to the distal end of the strain relief 236. In FIG. 2, the grip 228 is textured, for example with parallel ridges, to provide points of friction for the user while the probe 210 is rotated about the axis of the shaft 214 and inserted through nerve tissue at or near the neural pathway 204. In this embodiment, the ridges on grip the 228 can also be used to determine an angle of rotation of the apparatus. In one embodiment, the strain relief 236 can have a non-round (non-circular) cross-section, which can be square, triangular, or "toothed" like a mechanical gear. The strain relief 236 can be tapered with a larger distal outer diameter, in order to fit with the handle 216, and a smaller proximal outer diameter, in order to secure the electrical cable 238 and the flexible tubing 224. This taper provides increased grip for the user and reduces slipping of the user's fingers as the probe 210 is advanced into nerve tissue at or near a neural pathway 204. The strain relief 236 can provide a comfortable handle for the user and can conform to a user's gripping preference. In FIG. 2, an electrical cable 238 and flexible tubing 224 extend from the handle 216 and the strain relief 236 in parallel and adjacent each other. Notably, in this embodiment, the electrical cable 238 and the flexible tubing 224 do not extend from the handle 216 perpendicular to one another. This arrangement can provide a comfortable grasp and can enhance the ease of manipulation of the probe 210 during placement, rotation, insertion, etc.

In one particular embodiment, electrical energy can be supplied to the conductive region 212 from the controller 150 through the pulse generator 130 (FIG. 1) via an electrical coupling, comprising an electrical connector 240, an electrical cable 238 and the conductive shaft 214. All electrical contacts, except for the conductive region 212, can be isolated from the user by a connector pin housing located in the electrical connector 240. The electrical cable 238 can flexibly couple the controller 150 to the conductive shaft 214, which supplies energy to the conductive region 212 via the pulse generator 130 (FIG. 1). The electrical cable 238 can also relay temperature data back to the controller 150. In one particular embodiment, one conductor in the electrical cable 238 can act as both a thermocouple wire as well as an RF delivery wire. Utilizing a single conductor for both purposes reduces the overall mass of the electrical cable 238 and minimizes the forces and moments applied at the handle 216 during placement of probe in, near or around nerve tissue at a neural pathway 204. It will be understood by a person skilled in the art that separate cables and/or conductors may alternatively be used in conjunction with a temperature sensor.

In addition, a fluid delivery mechanism 210 can be flexibly coupled to a fluid delivery interface connection 226, and through it to the shaft 214 via flexible tubing 224, in order to allow the administration of a treatment composition to a region of tissue in a patient's body. Therefore, the probe 210 can be simultaneously connected to the fluid delivery mechanism 211 and the pulse generator 130 (FIG. 1) in order to treat a target nerve 220. The fluid delivery interface connection 226 can include any connector including, but not limited to, a luer type connector, that allows for the flow of fluid from the fluid delivery mechanism 211 to the flexible tubing 224.

In operation, the probe 210 is inserted into an area near a neural pathway 204 such as at a target nerve 220. Proper placement of the probe 210 can be confirmed by applying electrical energy using the conductive region 212 to stimulate the target nerve 220, as discussed in more detail below. An anesthetic fluid or another treatment composition can optionally be administered by actuating the fluid delivery mechanism 211. Apart from pharmacological agents, including anesthetics, the applied treatment composition can include, for example, a fluid that is electrically conductive or a fluid used to heat or cool the tissue if desired. The treatment composition can exit the fluid delivery mechanism 211 and flow through the fluid delivery interface connection 226, the flexible tube 224, and the lumen of the shaft 214 to the conductive region 212 where it exits through the aperture 222. The incorporation of a fluid delivery system into the probe 210 allows fluid delivery mechanism 211 to be pre-connected to fluid delivery interface connection 226, which can reduce the likelihood of inadvertent movement of the conductive region 212 by removing the requirement to use and therefore remove a separate apparatus to apply a treatment composition, which would generally result in an adjustment of the position of the conductive region 212. Additionally, the use of the flexible tube 224 can further decrease the forces acting on the handle 216 and the shaft 214 when the fluid delivery mechanism 211 is actuated to administer the treatment composition, for example, when a plunger on a syringe is depressed. Therefore, after stimulation to confirm proper placement of the probe 210, manual manipulation of the probe 210 is minimized and thus the likelihood of shifting the probe 210, and thus the conductive region 212, out of position is decreased. Moreover, the use of a probe 210 with a shaft 214 whose distal end is sharp or pointed allows the probe 210 to be inserted without the need to first insert a separate introducer tube or needle, thus further reducing the likelihood of positional shifting of the probe 210. However, an introducer can also be used and is considered to be within the scope of the invention.

After optionally administering a treatment composition, radio frequency (RF) energy can be applied to a target nerve 220 through conductive region 212. A return dispersive electrode 208 is provided to create a closed circuit when the probe 210 is electrically operated in contact with the target nerve 220. Since the fluid delivery mechanism 211 is still connected to the probe 210 during energy delivery, it is to be understood that delivery of treatment composition coincident with the delivery of energy is possible. During nerve stimulation and/or treatment, temperature sensor feedback can be used to automatically control the radiofrequency (RF) energy delivered to the target nerve 220 to help ensure safe operation of the probe 210 via controller the 150. For example, if the body tissue temperature increases rapidly while applying RF energy as measured by the temperature sensor feedback mechanism, RF energy delivery to the target nerve 220 can be suspended or reduced to provide a controlled ramp to the desired set temperature, such as based on which procedure or step is being performed. In this manner, the user does not blindly apply RF energy to the nerve tissue, but is informed in real-time of the effects that RF energy delivery has on tissue temperature.

In some embodiments, as has been previously described, the flexible tube 224 can provide the mechanical slack required to ensure that fluid delivery does not introduce added force to the probe 210. Other treatment tool(s) 242, depending on the procedure, can also be flexibly connected to probe 210. Probe 210 can therefore be provided with pre-formed connectors for these treatment tools that are flexibly coupled to probe the 210.

Figure 3:
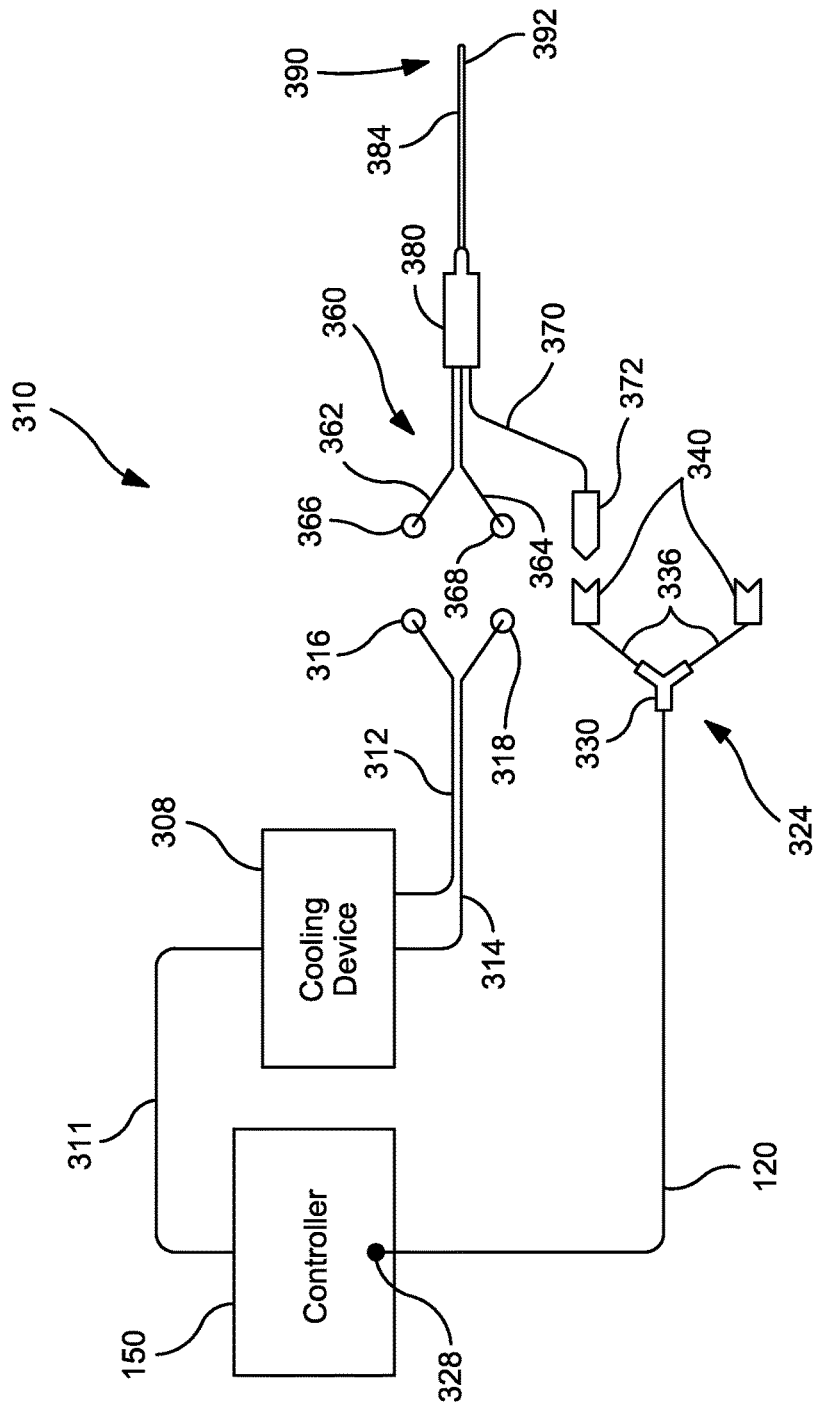
FIG. 3 is perspective side view of another exemplary probe utilized for stimulating a nerve, delivering electrical energy directly to the vicinity of a target nerve to block nerve fiber activity, and ablating the nerve.

FIG. 3 shows another embodiment of a suitable percutaneous probe 310. The probe 310 can be coupled to a controller 150 via a lead 120 and to one or more cooling devices 308 via a pump cable 311, one or more proximal cooling supply tubes 312, and one or more proximal cooling return tubes 314. The probe can also be coupled to a pulse generator 130 (FIG. 1) that is controlled by the controller 150. As shown in FIG. 3, a distal region 324 of the lead 120 can include a splitter 330 that can divide the lead 120 into two distal ends 336 such that the probe 310 can be connected to lead 120. Meanwhile, a proximal end 328 of the lead 120 is connected to controller 150. This connection can be permanent, whereby, for example, the proximal end 328 of the lead 120 is embedded within the controller 150, or temporary, where, for example, the proximal end 328 of the lead 120 can be connected to the controller 150 via an electrical connector. The two distal ends 336 of the lead 120 can also terminate in connectors 340 operable to couple to the probe 310 and establish an electrical connection between the probe 310 and the controller 150.

One or more cooling devices 308 can be used and can include any means of reducing a temperature of material located at and proximate to the probe 310. The cooling device 308 can include two peristaltic pumps operable to circulate a fluid from the cooling device 308 through one or more proximal cooling supply tubes 312, the probe 310, one or more proximal cooling return tubes 314 and back to the cooling devices 308. The fluid can be water or any other suitable fluid. In other embodiments, the cooling device 308 can include only one peristaltic pump or one or more electrothermal cooling devices or any other cooling means. The cooling device 308 can be operable to communicate at least uni-directionally, and optionally bi-directionally, with the controller 150. In this way, feedback control can be established between the cooling device 308 and the controller 150. The feedback control involves the controller 150, the probe 310, and the cooling device 308, although any feedback between any two devices is also contemplated. The feedback control can be implemented, for example, in a control module which may be a component of the controller 150. In this embodiment, the controller 150 can be operable to communicate bi-directionally with the probe 310 as well as with the cooling device 308, where bi-directional communication refers to the capability of a device to both receive a signal from and send a signal to another device.

As an example of feedback control, the controller 150 can receive temperature measurements from probe 310. For instance, based on the temperature measurements, the controller 150 can perform some action, such as modulating the power that is sent to the probe 310 from the pulse generator 130 (not shown). For example, power to the probe 310 could be increased when a temperature measurement is low or decreased when a measurement is high. In some cases, the controller 150 may terminate power to the probe 310. Thus, the controller 150 can receive a signal (e.g., temperature measurement) from the probe 310, determine the appropriate action, and send a signal (e.g., decreased or increased power) back to the probe 310. Alternatively, the controller 150 can send a signal to the one or more cooling devices 308 to either increase or decrease the flow rate or degree of cooling being supplied to the probe 310.

Alternatively, if one or more cooling devices 308 includes one or more peristaltic pumps, the one or more pumps can communicate a fluid flow rate to the controller 150 and may receive communications from the controller 150 instructing the pumps to modulate this flow rate. In some instances, the one or more peristaltic pumps can respond to the controller 150 by changing the flow rate or turning off for a period of time. With the cooling devices 308 are turned off, any temperature sensing elements associated with the probe 310 would not be affected by the cooling fluid, allowing a more precise determination of the surrounding tissue temperature to be made.

In still other embodiments, the one or more cooling devices 308 can reduce the rate of cooling or disengage depending on the distance between the probe 310. For example, when the distance is small enough such that a sufficient current density exists in the region to achieve a desired temperature, little or no cooling may be required. In such an embodiment, energy is preferentially concentrated between first and second energy delivery devices 392 through a region of nerve tissue to be treated, thereby creating a strip lesion. A strip lesion is characterized by an oblong volume of heated tissue that is formed when an active electrode is in close proximity to a return electrode of similar dimensions. This occurs because at a given power, the current density is preferentially concentrated between the electrodes and a rise in temperature results from current density.

One or more cooling devices 308 can also communicate with the generator 130 in order to alert the controller 150 to one or more possible errors and/or anomalies associated with one or more cooling devices 308, such as if cooling flow is impeded or if a lid of the one or more cooling devices 308 is opened. The generator 130 can then act on the error signal by at least one of alerting a user, aborting the procedure, and modifying an action.

In still other embodiments, the controller 150 can communicate with only one of the one or more cooling devices 308 or communication between devices may be unidirectional. For example, the one or more cooling devices 308 can be operable to receive incoming signals from the controller 150 but not to send signals back to the controller 150. In addition to the aforementioned feedback systems, the controller 150 can respond to evoked potentials (EP) by electroencephalography (EEG), electrocardiogram (ECG) measurements, electromyogram (EMG) measurements, or some other measure of patient response to a treatment procedure, as discussed below, and then respond accordingly.

As illustrated in FIG. 3, the means of facilitating communication between the one or more cooling devices 308 and the controller 150 can take the form of a pump cable 311 electrically connecting the controller 150 to the one or more cooling devices 308. In other embodiments, the controller 150 and the one or more cooling devices 308 can be connected with an RS-232 cable, a fiber optic cable, a USB cable, a Firewire™ (ieee 1394) cable or other means of electrical coupling. In yet further embodiments, communication between the controller 150 and the one or more cooling devices 308 can be achieved using some other communication protocol including but not limited to infrared, wireless, Bluetooth™ and others and the invention is not limited in this regard.

As illustrated in FIG. 3, the one or more proximal cooling supply tubes 312 can include proximal supply tube connectors 316 at the distal ends of the one or more proximal cooling supply tubes 312. Additionally, the one or more proximal cooling return tubes 314 can include proximal return tube connectors 318 at the distal ends of the one or more proximal cooling return tubes 314.

In one embodiment, the probe 310 can include a proximal region 360, a handle 380, a hollow elongate shaft 384, and a distal tip region 390 including energy delivery devices 392. The proximal region 360 can include a distal cooling supply tube 362, a distal supply tube connector 366, a distal cooling return tube 364, a distal return tube connector 368, a probe assembly cable 370, and a probe cable connector 372. In this embodiment, the distal cooling supply tube 362 and the distal cooling return tube 364 can be flexible to allow for greater maneuverability of the probe 310, but alternate embodiments with rigid tubes are possible.

In one embodiment, the proximal supply tube connector 316 can be operable to interlock with the distal supply tube connector 366 and the proximal return tube connector 318 can be operable to interlock with the distal return tube connector 368. This helps to establish a circuit within which a cooling fluid may flow while maintaining modularity of the probe 310.

In addition, in the embodiment illustrated in FIG. 3, the probe cable connector 372 can be located at a proximal end of the probe assembly cable 370 and can be operable to reversibly couple to one of connectors 340, thus establishing an electrical connection between the controller 150 and the probe 310. The probe assembly cable 370 can include one or more conductors depending on the specific configuration of the probe 310. For example, the probe assembly cable 370 can include five conductors allowing the probe assembly cable 370 to transmit RF current from a pulse generator 130 (FIG. 1), as determined by the controller 150, to the energy delivery device 392, as well as to connect multiple temperature sensing devices to the controller 150 as discussed below.

An energy delivery device 392 can include any means of delivering energy to a region of nerve tissue adjacent distal tip region 390. For example, the energy delivery device 392 can include radio frequency (RF) energy from a pulse generator 130, as discussed below. In one embodiment, the energy delivery device 392 includes an electrode. The active region of the electrode can be 2 millimeters (mm) to 20 mm in length and energy delivered by the electrode can be electrical energy in the form of current in the RF range. In some embodiments, feedback from the controller 150 can automatically adjust the exposed area of the energy delivery device 392 in response to a given measurement such as impedance or temperature. This can be accomplished through the use of an adjustable insulation sleeve associated with the energy delivery device 392. Adjustment of the insulation sleeve can be accomplished through sliding the sleeve proximally or distally along the energy delivery device. The adjustment can be done manually in other embodiments. Alternatively, additional conductive regions can be provided along the distal tip region 390 proximate the energy delivery device 392. In such an embodiment, the extent of nerve impairment, such as the size or shape of a lesion created during an ablation procedure, can be altered by selectively delivering energy through one or more of the additional conductive regions and the energy delivery device 392. Furthermore, one or more energy delivery devices 392 can include any combination of active electrodes and return electrodes, as is well known in the art.

It is to be understood that FIGS. 2 and 3 are examples of suitable probes that can be utilized. However, other suitable probes can be utilized and are described in U.S. Pat. No. 7,306,596 to Hillier, et al., U.S. Pat. No. 8,187,268 to Godara, et al., and U.S. Pat. No. 8,740,897 to Leung, et al., each of which is hereby incorporated by reference in its entirety. Further, it is also to be understood that more than one probe 310 can be utilized to deliver nerve stimulation to a target nerve, where multiple probes can be connected to multiple channels in the pulse generator (discussed below) for delivery of the nerve stimulation, where each channel can be used for treating a different location or source of chronic pain. For instance, a first probe can be connected to a first channel of a pulse generator to treat a first area of the upper back, a second probe can be connected to a second channel of a pulse generator to treat a second area of the back, a third probe can be connected to a third channel to treat a third area of the back, and a fourth probe can be connected to a fourth channel to treat a fourth area of the back.

Pulse Generator

Returning now to FIG. 1, the probe 110 can be connected to a pulse generator 130 through an electrical lead 120. In one embodiment, the pulse generator 130 can be a bipolar constant current stimulator. One exemplary stimulator is the DIGITIMER DS5 electrical stimulator available from Digitimer Ltd., England. Other constant current and constant voltage pulse generators may be used. Further, as indicated above, the pulse generator can include multiple channels to allow for the treatment of multiple sources or locations of chronic pain, where multiple probes are connected to the multiple channels. In this manner, each source or location of chronic pain can be treated at a different stimulation level if needed because each probe can deliver stimulation from the pulse generator via its own channel.

User Interface

The system can also utilize a user interface 140. This user interface 140 can be in the form of a computer that interacts with the controller 150 and can be powered by an isolation system 180, each described herein.

The computer operates software designed to record signals passed from the controller, and to drive the controller's output. Possible software includes Cambridge Electronic Design's (UK) SPIKE program. The software is programmable, can record and analyze electrophysiological signals such as EPs, EEG signals, ECG signals, and EMG signals, and can direct the controller to deliver stimulation.

Further, the user interface 140 can include a monitor 141, and the monitor can be configured to show multiple views via a display screen (not shown). For instance, a first view can display information related to identifying a source of chronic pain, a second view can display information related to verifying the source of chronic pain and the third view can display information related to treating chronic pain.

Patient Monitor System

A patient monitor system 160 can also be used in the system of the present invention. The patient monitoring system can acquire, amplify, and filter physiological signals, and can also output them to the controller 150. The system includes an electroencephalogram (EEG) monitor 170 to collect electrical signals, and specifically evoked potentials (EPs), from the brain. The electroencephalogram monitor 170 includes EEG electrodes 172 coupled with an alternating current (AC) amplifier 200A. The electrodes can be positioned on the scalp of a patient in any suitable manner known to one of ordinary skill in the art such that the electrical activity of any area of the brain can be monitored. In some embodiments, 3 to 128 electrodes can be utilized. For instance, 5, 16, 32, or 64 electrodes can be utilized to obtain EEG measurements via placement on the scalp or any other suitable location. Specifically, when a certain level of electrical energy is applied to an area near, around, or on a target nerve via a percutaneous probe, such as one of the probes discussed above and shown in FIGS. 2 and 3, EEG measurements of in any of area of the brain can be recorded to measure the amplitude of the corresponding evoked potential activity, the latency between the application of the electrical nerve stimulation and the onset of a first EPs, the latency between the end of one EP and the start of subsequent EPs, the frequency of each of the EPs when bursts of multiple EPs are present, and as the shape of the EPs. Through a quantitative analysis of this information at the low frequency electrical nerve stimulation, a target nerve associated with the neural pathway that is the source of chronic pain can be identified, after which the target nerve can be blocked and impaired to treat the chronic pain.

Figure 4A:
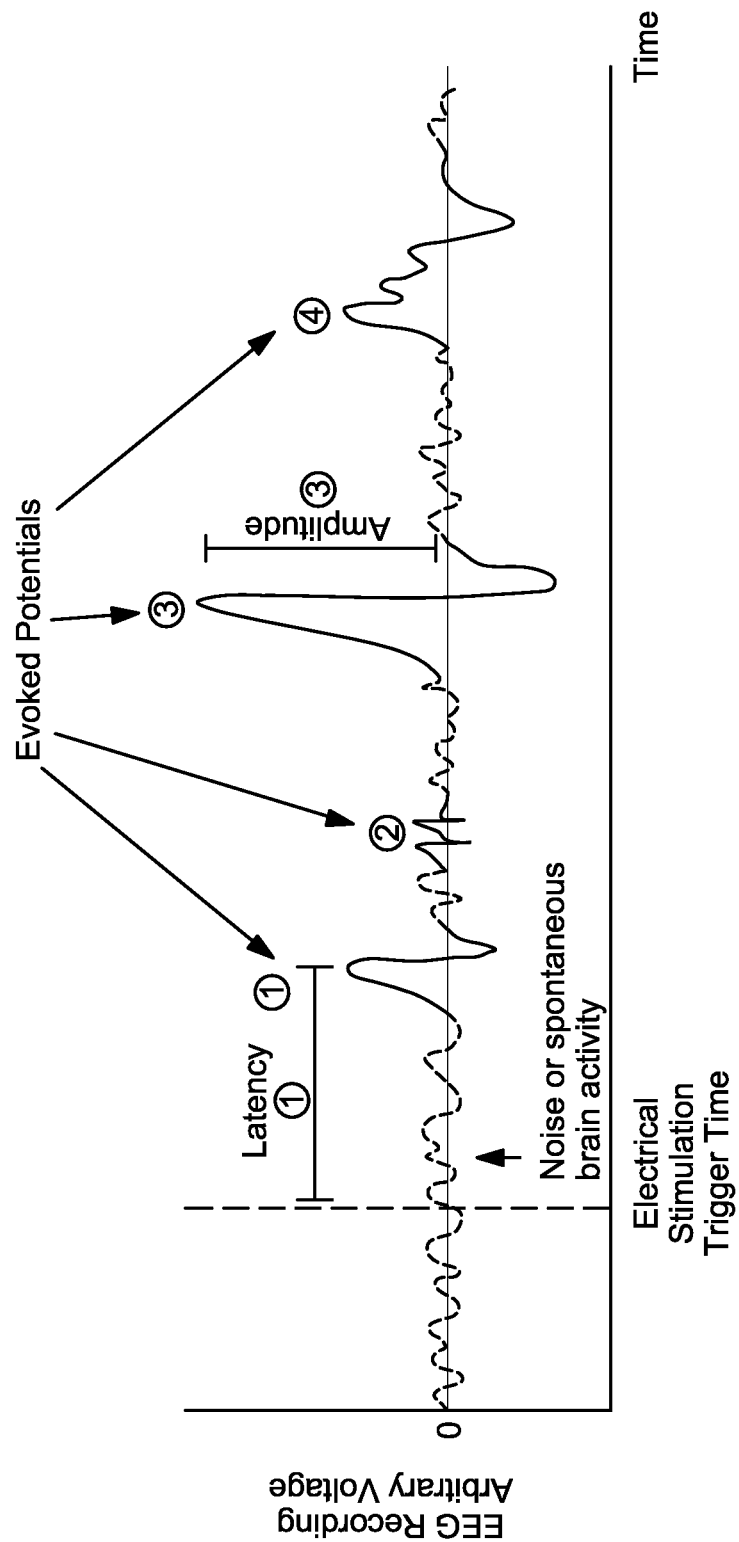
FIG. 4(*a*) is a graph showing evoked potentials with various amplitudes, latencies, and shapes. The dashed line indicates the trigger time, or the onset of a stimulation pulse.

FIG. 4(a) is graph showing the amplitude, latency and shape of several evoked potentials (1-4). The potentials are elicited by an electrical stimulation that is indicated in time as a vertical dashed line. If the stimulation intensity is constant, then the evoked potential amplitude of an individual burst will increase as the distance between the probe and nerve decreases, helping the physician drive the probe towards the painful circuitry. Alternatively, the amplitude of the evoked potential will decrease with increasing distance between the probe and nerve.

Again, the amplitude, latency, frequency, and shape of an EP can help in locating a neural pathway associated with chronic pain based on the location of the brain wave monitoring. For instance, observation of EP activity in one or more predetermined regions of the brain upon nerve stimulation can indicate that the target nerve being stimulated is part of the neural pathway associated with chronic pain. Further, in another embodiment, the observation of an EP of sufficient amplitude, latency, frequency, or shape at a predetermined stimulation means, level, or parameter can indicate that the target nerve being stimulated via the probe is in close enough proximity to a part of the neural pathway associated with chronic pain in order to treat the chronic pain at the target nerve.

Figure 4B:
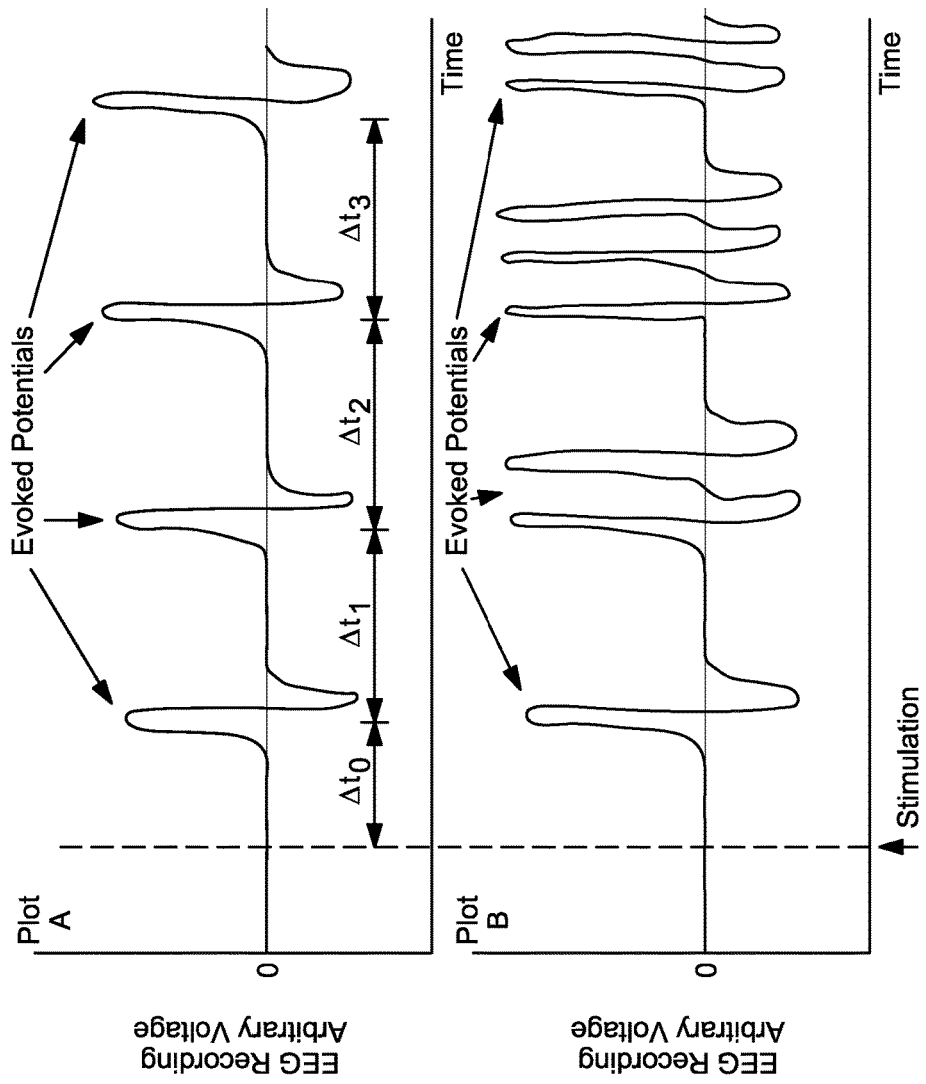

FIG. 4(b) demonstrates multiple evoked potentials activated by a single stimulation. It is thought that chronic pain may be discernible from acute pain by the existence of repeating potentials. In Plot A, the stimulation elicited evoked potential has a latency of $\Delta t_0$, and, as shown, the same neuron continues to fire at regular intervals (e.g., $\Delta t_1 = \Delta t_2 = \Delta t_3$), approximating a long-lasting neural oscillation or volley. Plot B demonstrates a phenomenon known as "wind-up", where evoked potentials occur repetitiously, but each occurrence demonstrates a new number of potentials and activation frequencies.

Figure 4C:
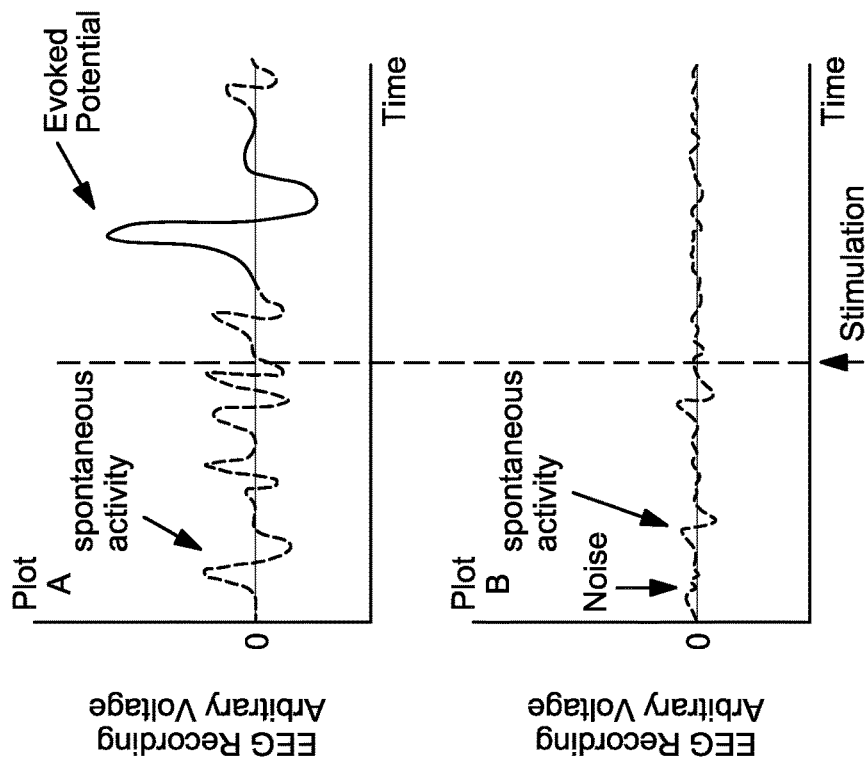

FIG. 4(c) demonstrates a pre-ablation (Plot A) and post-ablation (Plot B) data segment. In Plot A, the data tracing is described by spontaneous or baseline EEG activity and electrical noise, and a stimulus-elicited evoked potential. Following ablation of the nerve, the spontaneous activity recorded by the EEG system is reduced in amplitude and frequency, and stimulation (vertical dashed line) is incapable of eliciting an evoked potential.

In the embodiments discussed above, because of the high temporal resolution of the EEG measurements, the determination as to which nerve is associated with the neural pathway responsible for the chronic pain experienced by the patient can be made in real-time, as chronic pain is elicited by the probe/EEG system.

In addition to the aforementioned EEG monitor 170, the patient monitoring system 160 can also include a heart-rate monitor 180 to collect electrocardiogram (ECG) signals, and a muscle activity monitor 190 to collect electromyography (EMG) signals. The heart-rate monitor 180 can include ECG electrodes 182 coupled with an alternating current (AC) amplifier 200B. Meanwhile, the muscle activity monitor 190 can include EMG electrodes 192 coupled with an AC amplifier 200C. Other types of transducers can also be used depending on which physiological parameters are to be monitored. As described, all physiological signals obtained with the patient monitoring system are passed through an AC signal amplifier/conditioner (200A, 200B, 200C). One possible amplifier/conditioner is Model LP511 AC amplifier available from Grass Technologies, a subsidiary of Astro-Med, Inc., West Warwick, R.I., USA.

Isolated Power System

All instruments can be powered by an isolated power supply or system 194 to protect such instruments from ground faults and power spikes carried by the electrical main. One example of an isolated power system is available is the Model IPS115 Isolated Medical-grade Power System from Grass Technologies, a subsidiary of Astro-Med, Inc., West Warwick, R.I., USA.

Controller

A controller 150 is used that can record waveform data and digital information from the patient monitor system 160, such as EEG data, ECG data, EMG data, RF temperature data, etc., and can generate waveform and digital outputs simultaneously for real-time control of the pulse generator 130. The controller 150 can have onboard memory to facilitate high speed data capture, independent waveform sample rates and on-line analysis. An exemplary controller 150 may be a POWER 1401 data-acquisition interface unit available from Cambridge Electronic Design (UK).

Electrical Stimulation Parameters

In the present invention, different electrical stimulation parameters are used based on the goal of the stimulation. The various stimulation parameters contemplated by the present invention are discussed individually in more detail below.

First (Low Frequency) Electrical Nerve Stimulation to Elicit Chronic Pain

First, in order to elicit a chronic pain response in a target nerve that is suspected of or could be associated with a neural pathway that is the source of a patient's chronic pain, as determined by the presence of or a change in EP activity observed via EEG during brain wave monitoring (i.e., an increase in amplitude of the EPs, a decrease in latency, an increase in frequency, or a sufficient change in shape), low frequency electrical nerve stimulation parameters are utilized. The first (low frequency) electrical nerve stimulation can be delivered at a constant waveform, pulse duration, frequency, intensity, or a combination thereof, such as at a constant-current, or at a constant voltage. Generally speaking, the use of current regulated stimuli has an advantage over voltage regulated stimuli in certain situations because the current density can be better controlled. In addition, the stimulation can be delivered in a monophasic or biphasic fashion. Further, the waveform can be a square wave, sinusoidal, or a pulse train.

Moreover, the frequency at which the first (low frequency) electrical nerve stimulation is applied is typically about 100 Hertz (Hz) or less. For instance, the frequency at which the first (low frequency) electrical nerve stimulation is applied can range from about 0.1 Hz to about 100 Hz, such as from about 0.1 Hz to about 75 Hz, such as from about 0.1 Hz to about 50 Hz. Moreover, the pulse duration can range from about 0.01 milliseconds (ms) to about 10 ms, such as from about 0.05 ms to about 5 ms, such as from about 0.1 ms to about 2.5 ms. In addition, for biphasic pulses, the phase duration can range from about 0.005 ms to about 5 ms, such as from about 0.025 ms to about 2.5 ms, such as from about 0.05 ms to about 1.25 ms for each portion of the pulse. Furthermore, the current applied can range from about 0.01 milliAmps (mA) to about 50 mA, such as from about 0.25 mA to about 40 mA, such as from about 0.2 mA to about 30 mA. Also, the pulse period, which is the amount of time between the start of one pulse to the start of the next pulse and includes phase duration, intrapulse intervals, and interpulse intervals, can range from about 0.01 milliseconds (ms) to about 20 ms, such as from about 0.05 ms to about 20 ms, such as from about 0.1 ms to about 5 ms. In addition to the aforementioned frequency and current (intensity) ranges, other combinations of frequency and current ranges are contemplated by the present invention as understood by a person having ordinary skill in the art.

Second (High Frequency) Electrical Nerve Stimulation for Blocking

Next, in order to further verify that the target nerve has been correctly identified as part of the neural pathway that is the source of chronic pain through the first (low frequency) electrical nerve stimulation and EEG measurements of EP activity discussed above, a second (high frequency) electrical nerve blocking stimulation can be performed. Such a high frequency electrical nerve blocking stimulation can temporarily block the passage of impulses along a neuron's axon to verify that the correct nerve (i.e., the nerve associated with the chronic pain response) has been identified as part of the neural pathway that is the source chronic pain observed via EEG in the brain during the first (low frequency) electrical nerve stimulation. Confirmation that the correct nerve has been identified as part of the neural pathway that is the chronic pain source can be made if brain wave activity consistent with an effective nerve block is observed. For instance, significant reduction or silencing of spontaneous chronic pain activity or EP amplitude in response to the high frequency electrical nerve blocking stimulation delivered to the target nerve can indicate that the target nerve is associated with the source of the chronic pain and has been correctly identified, as can an increase in latency between the time of stimulation and the onset of an EP, an increase in the latency between multiple EPs, a decrease in the frequency of the EPs, or a significant change in shape of the EPs. Meanwhile, confirmation that the target nerve is not a part of the neural pathway associated with chronic pain can be made if brain wave activity (e.g., EPs) inconsistent with an effective nerve block is observed. For instance, if no significant reduction of spontaneous chronic pain activity or an increase of the amplitude of the EPs is observed in response to the second (high frequency) electrical nerve blocking stimulation delivered to the target nerve, this can indicate the target nerve being stimulated is not associated with the source of the chronic pain. Likewise, little to no change in the latency from the time of the application of the nerve stimulation to the onset of a first evoked potential, little to no change in the latency between multiple EPs, or little to no change in EP shape can indicate that the target nerve being stimulated is not associated with the source of the chronic pain.

The second (high frequency) electrical nerve stimulation can be applied at a constant waveform, pulse duration, frequency, intensity, or a combination thereof, such as a constant-current, or at a constant-voltage. In addition, the stimulation can be delivered in a monophasic or biphasic (most desirable) fashion. Further, the waveform can be a square wave, a sinusoidal wave, or a pulse train, where bursts of multiple pulses may be delivered on the order of milliseconds to seconds and where each pulse train is separated by an off time which is the interburst interval (variable, patient specific). Generally, the frequency at which the high frequency electrical nerve blocking stimulation is applied ranges from about 1,000 Hz to about 100,000 Hz. For instance, the frequency can range from about 1,500 Hz to about 90,000 Hz, such from about 2,000 Hz to about 80,000 Hz, such as from about 2,500 Hz to about 70,000 Hz. Moreover, the pulse duration can range from about 5 microseconds (μs) to about 500 μs, such as from about 10 μs to about 400 μs, such as from about 20 μs to about 300 μs. In addition, for biphasic pulses, the phase duration can range from about 2.5 microseconds (μs) to about 250 μs, such as from about 10 μs to about 200 μs, such as from about 20 μs to about 100 μs for each portion of the pulse. Furthermore, the current applied can range from about 0.01 mA to about 50 mA, such as from about 0.25 mA to about 40 mA, such as from about 0.2 mA to about 30 mA. Also, the pulse period can range from about 10 μs to about 1000 μs, such as from about 20 μs to about 800 μs, such as from about 40 μs to about 600 μs. In addition to the aforementioned frequency and current (intensity) ranges, other combinations of frequency and current ranges are contemplated by the present invention as understood by a person having ordinary skill in the art.

Third (Ultra-High Frequency) Electrical Nerve Stimulation for Ablation

Once the target nerve has been identified via the first (low frequency) electrical nerve stimulation and EEG measurements discussed above as the part of the neural pathway that is the source of chronic pain, and, optionally, verification that the target nerve has been correctly identified as part of the neural pathway associated with chronic pain via the second (high frequency) electrical nerve blocking stimulation also discussed above, the neural pathway determined to be responsible for a patient's chronic pain can be impaired to prevent transmission of the corresponding pain signal to the brain. For example, the neural pathway can be ablated using a third (ultra-high frequency) electrical nerve stimulation such as an ablation, where a lesion is formed at or near the neural pathway. However, it is also to be understood that any other suitable impairment method other than ablation can also be utilized. For instance, rather than ablation, a pulsed RF stimulation can be applied to alter or impair the neural pathway.

The third (ultra-high frequency) electrical nerve stimulation can be delivered in a constant-current, or a constant-voltage fashion. The waveform can be a square wave, a sinusoidal wave, or one or more impulses. Generally, the frequency at which the third (ultra-high frequency) electrical nerve stimulation is carried out is at least about 100,000 Hz. For instance, the frequency can range from about 100,000 Hz to about 1.5 Megahertz (MHz), such as from about 200,000 Hz to about 1 MHz, such as from about 300,000 Hz to about 800,000 Hz. Moreover, the pulse duration can range from about 0.5 microseconds (μs) to about 5 μs, such as from about 1 μs to about 4 μs, such as from about 2 μs to about 3 μs. Furthermore, the current applied can have an amplitude of less than about 1.4 Amps, such as from about 0.01 Amps to about 1.4 Amps, such as from about 0.05 Amps to about 1.2 Amps, such as from about 0.1 Amps to about 1 Amp.

Also, the pulse period can range from about 1 μs to about 10 μs, such as from about 2 μs to about 8 μs, such as from about 5 μs to about 6 μs. In addition to the aforementioned frequency and current (intensity) ranges, other combinations of frequency and current ranges are contemplated by the present invention as understood by a person having ordinary skill in the art.

Other suitable nerve impairment/nerve ablation techniques are described in U.S. Pat. No. 7,306,596 to Hillier, et al., U.S. Pat. No. 7,819,869 to Godara, et al., U.S. Pat. No. 7,824,404 to Godara, et al., U.S. Pat. No. 8,518,036 to Leung, et al., and U.S. Pat. No. 8,740,897 to Leung, et al., each of which is hereby incorporated by reference in its entirety.

After the nerve has been impaired as discussed above, the first (low frequency) electrical nerve stimulation, the second (high frequency) electrical nerve stimulation, or both can be repeated to verify that significantly reduced or no evoked potential activity associated with chronic pain is being recorded by the EEG in the area of the brain associated with chronic pain in response to the electrical stimulation, where such additional electrical stimulations can confirm successful impairment of the neural pathway and/or target nerve associated with the chronic pain. For instance, if the EP amplitude and frequency are significantly decreased, or if the latency is increased, successful impairment can be confirmed. Similarly, a significant change in shape of the EP can confirm successful impairment.

Figure 6:
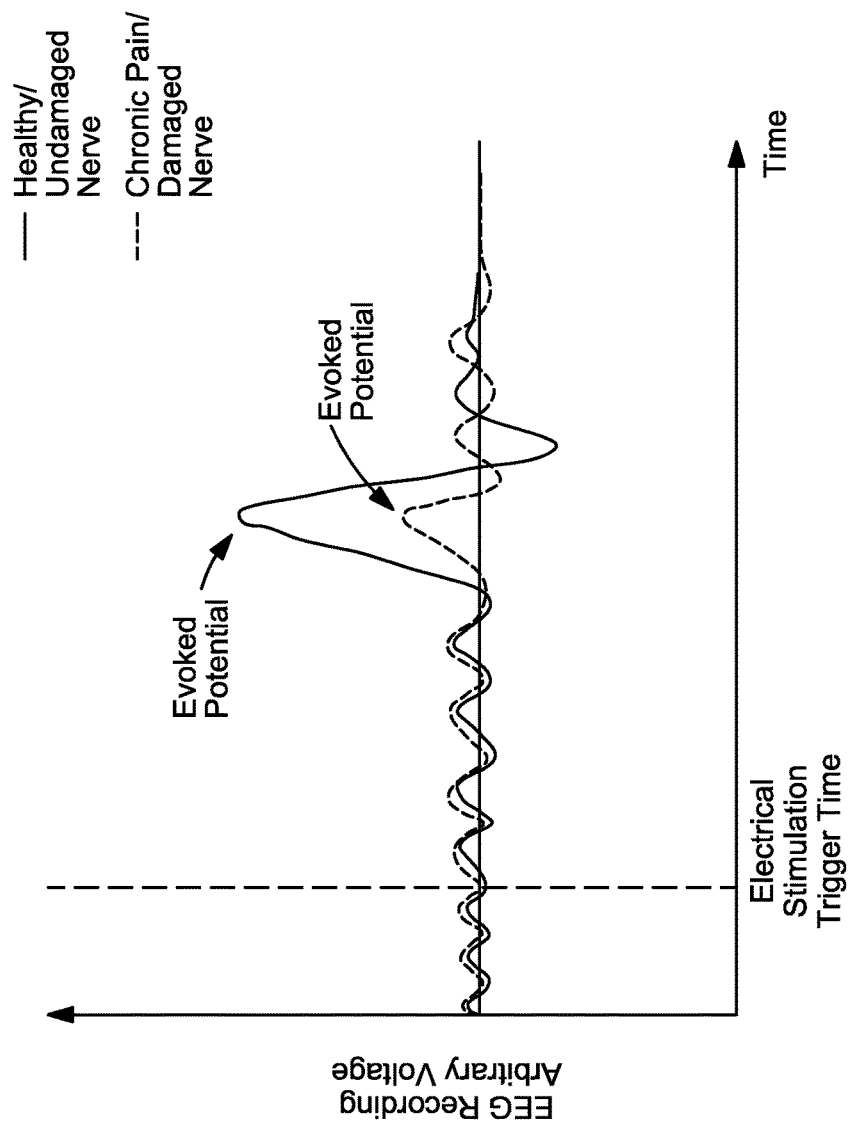
FIG. 6 is a graph comparing an evoked potential elicited by a single stimulation (vertical dashed line) of a healthy nerve (solid waveform) with a nerve associated with chronic pain (dashed waveform).

Fourth (Additional) Electrical Nerve Stimulation of Additional Nerve for Reference If desired and as discussed above, an additional nerve besides the target nerve that is suspected of being a source of chronic pain can be stimulated to elicit a response that can serve as a reference response and can be compared to the response elicited upon the first electrical nerve stimulation of the target nerve, where such additional stimulation can serve as a means of verifying that the target nerve is part of the neural pathway associated with chronic pain. Such a comparison of elicited responses (e.g., evoked potentials) is shown in FIG. 6, which compares an evoked potential elicited by a single stimulation (vertical dashed line) at the site of a healthy nerve (solid waveform) with a nerve suspected of being associated with chronic pain (dashed waveform). As shown, the waveforms have different shapes, amplitudes, etc., and these differences indicate that the target nerve suspected of being a source of chronic pain is part of the neural pathway associated with chronic pain since it has a smaller amplitude compared to the evoked potential associated the healthy nerve (i.e., the additional nerve that is not associated with chronic pain).

To conduct such a comparison/verification where the elicited response or evoked potential for the additional nerve serves as a reference response to compare to an elicited response associated with a target nerve suspected of being the source of chronic pain, the controller can be configured to deliver an additional nerve stimulation to an additional nerve via the probe, wherein the additional nerve is not suspected of being a source of chronic pain, wherein the additional nerve stimulation is sufficient to elicit a response in the brain, further wherein the controller is configured to monitor for baseline activity in the brain, evoked potential activity in the brain as a result of the additional nerve stimulation, or both via the electroencephalography electrodes. Further, the elicited response from the additional nerve stimulation can be compared to the elicited response from the first nerve stimulation to verify that the target nerve is correctly identified as part of the neural pathway associated with chronic pain, wherein a difference in the elicited response from the additional nerve stimulation compared to the elicited response from the first nerve stimulation indicates that the target nerve is part of the neural pathway associated with chronic pain.

In order to elicit a response in an additional nerve that is not suspected of being be associated with a neural pathway that is the source of a patient's chronic pain in order to create a reference for comparison to a target nerve that is suspected of being associated with a neural pathway that is the source of a patient's chronic pain in order to verify that the correct target nerve has been located, as determined by the presence of or a change in EP activity observed via EEG during brain wave monitoring (i.e., an increase in amplitude of the EPs, a decrease in latency, an increase in frequency, or a sufficient change in shape), low frequency electrical nerve stimulation parameters are utilized. The additional electrical nerve stimulation can be delivered at a constant waveform, pulse duration, frequency, intensity, or a combination thereof, such as at a constant-current, or at a constant voltage. Generally speaking, the use of current regulated stimuli has an advantage over voltage regulated stimuli in certain situations because the current density can be better controlled. In addition, the stimulation can be delivered in a monophasic or biphasic fashion. Further, the waveform can be a square wave, sinusoidal, or a pulse train.

Moreover, the frequency at which the additional (fourth) electrical nerve stimulation is applied is typically about 100 Hertz (Hz) or less. For instance, the frequency at which the additional (fourth) electrical nerve stimulation is applied can range from about 0.1 Hz to about 100 Hz, such as from about 0.1 Hz to about 75 Hz, such as from about 0.1 Hz to about 50 Hz. Moreover, the pulse duration can range from about 0.01 milliseconds (ms) to about 10 ms, such as from about 0.05 ms to about 5 ms, such as from about 0.1 ms to about 2.5 ms. In addition, for biphasic pulses, the phase duration can range from about 0.005 ms to about 5 ms, such as from about 0.025 ms to about 2.5 ms, such as from about 0.05 ms to about 1.25 ms for each portion of the pulse. Furthermore, the current applied can range from about 0.01 milliAmps (mA) to about 50 mA, such as from about 0.25 mA to about 40 mA, such as from about 0.2 mA to about 30 mA. Also, the pulse period, which is the amount of time between the start of one pulse to the start of the next pulse and includes phase duration, intrapulse intervals, and interpulse intervals, can range from about 0.01 milliseconds (ms) to about 20 ms, such as from about 0.05 ms to about 20 ms, such as from about 0.1 ms to about 5 ms. In addition to the aforementioned frequency and current (intensity) ranges, other combinations of frequency and current ranges are contemplated by the present invention as understood by a person having ordinary skill in the art.

In addition to the method and system discussed above, the present invention also encompasses a kit for carrying out the various procedures outlined above. FIG. 5 depicts a kit 400 that includes any manner of suitable container 402 in which is provided any combination of the components depicted in FIGS. 1 through 3. It should be appreciated that the kit 400 need not contain all of the articles depicted in FIGS. 1 through 3. That is, components such as controller, pulse generator, user interface, patient monitoring system, amplifiers or the like need not be included—although suitable electrodes such as the EEG electrodes 172, ECG electrodes 182, and EMG electrodes 192 may be included in the kit.

The container 402 may be, for example, a suitable tray having a removable sealed covering in which the articles are contained. For example, an embodiment of the kit 400 can include the container 402 with one or more probes 110 and electrical leads 120 as discussed above.

The present invention encompasses a kit with any combination of the items utilized to perform the procedure of delivering various frequency levels of electrical nerve stimulation through a percutaneous probe inserted through the skin such that it can be in close proximity to a target nerve thought to be associated with a neural pathway responsible for or the source of chronic pain. For example, the kit 400 may include additional items, such as a drape, site dressings, tape, skin-markers and so forth. The kit 400 may include pre-packaged wipes 406 such as antiseptic wipes or skin-prep wipes.

Chronic Pain Identification, Verification, and Treatment Method

The present invention also encompasses a method for identifying, verifying the location of, and/or treating chronic pain. The method can include identifying a target nerve thought to be associated with a neural pathway that is the source of chronic pain, verifying that the target nerve has been correctly identified as part of the neural pathway associated with chronic pain, impairing the nerve, and verifying that the target nerve has been successfully impaired. The various steps for carrying out this method are discussed in more detail below.

For example, the method can involve a user, such as a doctor, nurse practitioner, nurse, technician, etc., advancing a percutaneous probe through the surface of the skin and towards a target nerve, which is a nerve that is suspected of being the source of a patient's chronic pain. Next, once the tip of the probe is close to the target nerve, a first (low frequency) electrical nerve stimulation (see parameters described above) can be delivered to the target nerve via a pulse generator or other suitable means through the probe. At this time, EEG signals can be recorded via electrodes to monitor evoked potential activity in one or more predetermined regions of the brain. During this time, the controller will analyze the signals and data received and will return to the user the strength and correlation of the detected nerve stimulation-elicited evoked potentials (EPs). Generally, as the distance between the probe and the chronic pain source decreases, the size (amplitude) and/or correlation of the one or more EEG-recorded EPs in the brain will increase, as will the frequency of the EPs when multiple EPs are present. Meanwhile, the latency between the stimulation and the onset of a first EPs will decrease as the distance between the probe and the source of the chronic pain decreases. Likewise, the latency between the end of one EP and the start of another EP can be decreased when the distance between the probe and the chronic pain source decreases. Further, the shape of the EPs can change, as demonstrated and discussed above in reference to FIG. 4(a).

Once the correlation is sufficient, such as when a sufficient amplitude, latency, frequency, or shape has been reached for the observed EPs, the user can be notified that the probe is in a location that is source of the chronic pain and that the location is a suitable location for blocking and/or impairing the target nerve. For instance, before impairing the nerve, a second (high frequency) electrical nerve stimulation (e.g., a nerve blocking stimulation) (see parameters described above) can be delivered to the target nerve, such as via the pulse generator, to temporarily prevent the transmission of impulses along the nerve, at which point, if the correct nerve has been identified as being associated with the source of the chronic pain, the EPs as measured by the EEG will be silenced or significantly reduced.

If the stimulation characteristics of the second (high frequency) electrical nerve blocking stimulation are sufficient to verify that the source of the chronic pain has been correctly identified, then, in one particular embodiment, the volume of nerve tissue that can be impaired or ablated at the probe's current setting can then be determined. If the nerve falls within that volume, then EPs and spontaneous or baseline activity carrying the chronic pain signals to the area of the brain being monitored can be silenced upon impairment or ablation through a third (ultra-high frequency) electrical nerve stimulation, and the patient will not feel any chronic pain post-ablation.

Further, the method contemplated by the present invention can include delivering an additional nerve stimulation to an additional nerve via the probe, wherein the additional nerve is not suspected of being a source of chronic pain, wherein the additional nerve stimulation is sufficient to elicit a response in the brain; and monitoring for baseline activity in the brain, evoked potential activity in the brain as a result of the additional nerve stimulation, or both via the electroencephalography electrodes. Further, the method can also include comparing the elicited response from the additional nerve stimulation to the elicited response from the first nerve stimulation to verify that the target nerve is correctly identified as part of the neural pathway associated with chronic pain, wherein a difference in the elicited response from the additional nerve stimulation compared to the elicited response from the first nerve stimulation indicates or verifies that the target nerve is part of the neural pathway associated with chronic pain.

After such verification as described above is complete, the user can then ablate the nerve via the third ultra-high frequency electrical nerve ablation parameters described above. Next, sufficient impairment or ablation can be verified by repeating the first (low frequency) electrical nerve stimulation, the second (high frequency) electrical nerve stimulation, or both. If no or significantly reduced EPs are recorded by the EEG system in the brain upon such electrical stimulation, then it can be concluded that the target nerve was successfully impaired or ablated. On the other hand, if the target nerve has not been successfully located, such as would be the case if the EPs in the brain were not silenced or significantly reduced upon repetition of the first electrical nerve stimulation, the second electrical nerve blocking stimulation, or both, then the user can continue the same procedure discussed above on additional target nerves until the nerve responsible for or associated with the neural pathway that is the cause of the chronic pain is successfully located.

While the present invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A system for identifying a neural pathway associated with chronic pain via nerve stimulation and brain wave monitoring of a mammalian brain, the system comprising:
   a probe, wherein the probe is positioned near an area that is suspected of being a source of chronic pain;
   electroencephalography electrodes; and
   a controller coupled to the probe and the electroencephalography electrodes, wherein the controller is configured to deliver a first nerve stimulation to a target nerve via the probe, wherein the target nerve is suspected of being a source of chronic pain, wherein the first nerve stimulation is sufficient to elicit a chronic pain response in the brain, further wherein the controller is configured to monitor for baseline brain activity, evoked potential activity in the brain as a result of the first nerve stimulation, or both via the electroencephalography electrodes,
   wherein the system monitors for evoked potential activity by measuring at least one of the following values;
   (i) evoked potential amplitude, wherein an increase in evoked potential amplitude indicates the probe is positioned closer to the source of the chronic pain and a decrease in evoked potential amplitude indicates the probe is positioned farther away from the source of the chronic pain;
   (ii) evoked potential latency, wherein a decrease in evoked potential latency indicates the probe is positioned closer to the source of the chronic pain and an increase in evoked potential latency indicates the probe is positioned farther away from the source of the chronic pain; and
   (iii) evoked potential frequency, wherein an increase in evoked potential frequency indicates the probe is positioned closer to the source of the chronic pain and decrease in evoked potential frequency indicates the probe is positioned farther away from the source of the chronic pain.

2. The system of claim 1, wherein the system monitors for evoked potential activity in one or more predetermined regions of the brain, wherein the presence of evoked potential activity in the one or more predetermined regions of the brain indicates the target nerve is part of the neural pathway associated with chronic pain.

3. The system of claim 1, wherein the system monitors for evoked potential activity by measuring evoked potential amplitude.

4. The system of claim 1, wherein the system monitors for evoked potential activity by measuring evoked potential latency.

5. The system of claim 1, wherein the system monitors for evoked potential activity by measuring evoked potential frequency.

6. The system of claim 1, wherein the system monitors for evoked potential activity in one or more predetermined regions of the brain, wherein the presence of evoked potential activity with a predetermined amplitude, a predetermined latency, a predetermined frequency, a predetermined shape, or a combination thereof in one or more predetermined regions of the brain indicates the target nerve is part of the neural pathway associated with chronic pain.

7. The system of claim 1, wherein the system monitors for evoked potential activity by measuring evoked potential amplitude, evoked potential latency, evoked potential frequency, evoked potential shape, or a combination thereof, wherein observation of an evoked potential with sufficient amplitude, latency, frequency, shape, or a combination thereof at a predetermined stimulation indicates the target nerve is in close enough proximity to a part of the neural pathway associated with chronic pain for treatment of the chronic pain.

8. The system of claim 7, wherein the controller is configured to:

deliver a second nerve stimulation via the probe at a location along the target nerve where the evoked potential activity with sufficient amplitude, latency, frequency, shape, or a combination thereof is observed, wherein the second nerve stimulation is sufficient to create a nerve block;

monitor brain wave activity as the second nerve stimulation is delivered;

confirm the target nerve has been correctly identified as part of the neural pathway associated with chronic pain if brain wave activity consistent with an effective nerve block is observed during application of the nerve block; and determine that the target nerve is not a part of the neural pathway associated with chronic pain if brain wave activity inconsistent with an effective nerve block is observed during the nerve block.

9. The system of claim 8, wherein the system treats chronic pain when the target nerve is correctly identified as part of the neural pathway associated with chronic pain, wherein the controller is configured to deliver a third nerve stimulation from the probe at the location along the target nerve where the evoked potential activity with sufficient amplitude, latency, frequency, shape, or a combination thereof is observed, wherein the third nerve stimulation is sufficient to impair the neural pathway associated with the chronic pain.

10. The system of claim 9, wherein the controller is further configured to verify impairment of the neural pathway is complete by repeating the first nerve stimulation, the second nerve stimulation, or both to confirm effective impairment of the target nerve, wherein impairment is complete if brain wave activity consistent with effective impairment of the neural pathway is observed.

11. The system of claim 1, wherein the controller is configured to deliver an additional nerve stimulation to an additional nerve via the probe, wherein the additional nerve is not suspected of being a source of chronic pain, wherein the additional nerve stimulation is sufficient to elicit a response in the brain, further wherein the controller is configured to monitor for baseline brain activity, evoked potential activity in the brain as a result of the additional nerve stimulation, or both via the electroencephalography electrodes.

12. The system of claim 11, wherein the elicited response from the additional nerve stimulation is compared to the elicited response from the first nerve stimulation to verify that the target nerve is correctly identified as part of the neural pathway associated with chronic pain, wherein a difference in the elicited response from the additional nerve stimulation compared to the elicited response from the first nerve stimulation indicates that the target nerve is part of the neural pathway associated with chronic pain.

13. The system of claim 1, wherein the probe is a percutaneous probe.

14. The system of claim 1, wherein the first nerve stimulation is electrical and is delivered at a frequency of about 100 Hertz or less and at an amplitude ranging from about 0.01 milliAmps to about 50 milliAmps.

15. The system of claim 8, wherein the second nerve stimulation is electrical and is delivered at a frequency ranging from about 1,000 Hertz to about 100,000 Hertz and at an amplitude ranging from about 0.01 milliAmps to about 50 milliAmps.

16. The system of claim 9, wherein the third nerve stimulation is electrical and is delivered at a frequency ranging from about 100,000 Hertz to about 1.5 Megahertz and at an amplitude of up to about 1.4 Amps.

17. The system of claim 1, wherein the controller transmits the first nerve stimulation and one or more additional nerve stimulations to the probe via a pulse generator connected to the probe via an electrical lead.

* * * * *